US012606625B2

(12) United States Patent
Lee et al.

(10) Patent No.: US 12,606,625 B2
(45) Date of Patent: **\*Apr. 21, 2026**

(54) ANTIBODY BINDING SPECIFICALLY TO B7—H3 AND USE THEREOF

(71) Applicants: Y-BIOLOGICS INC., Daejeon (KR); IntoCell, Inc., Daejeon (KR)

(72) Inventors: Hyun Ju Lee, Daejeon (KR); Eun-Young Shim, Daejeon (KR); Yunjung Ko, Daejeon (KR); Jin-Chul Youn, Daejeon (KR); Jae Eun Park, Daejeon (KR); Soo A Choi, Daejeon (KR); Seok Ho Yoo, Daejeon (KR); Dong Jung Lee, Daejeon (KR); Yeung-Chul Kim, Daejeon (KR); Youngja Song, Daejeon (KR); Jisu Lee, Daejeon (KR); Ju-Ry Lim, Daejeon (KR); Bum-Chan Park, Daejeon (KR); Young Woo Park, Daejeon (KR)

(73) Assignees: Y-BIOLOGICS INC., Daejeon (KR); IntoCell, Inc., Daejeon (KR)

( * ) Notice: Subject to any disclaimer, the term of this patent is extended or adjusted under 35 U.S.C. 154(b) by 1163 days.

This patent is subject to a terminal disclaimer.

(21) Appl. No.: 17/594,523

(22) PCT Filed: Jul. 8, 2020

(86) PCT No.: PCT/KR2020/008928
§ 371 (c)(1),
(2) Date: Oct. 20, 2021

(87) PCT Pub. No.: WO2021/006619
PCT Pub. Date: Jan. 14, 2021

(65) Prior Publication Data
US 2022/0348663 A1 Nov. 3, 2022

(30) Foreign Application Priority Data
Jul. 9, 2019 (KR) ........................ 10-2019-0082492

(51) Int. Cl.
*C07K 16/28* (2006.01)
*A61P 29/00* (2006.01)

(52) U.S. Cl.
CPC .......... *C07K 16/2827* (2013.01); *A61P 29/00* (2018.01); *C07K 2317/31* (2013.01); *C07K 2317/565* (2013.01); *C07K 2317/77* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| | | | |
|---|---|---|---|
| 9,371,395 | B2 | 6/2016 | Takahashi et al. |
| 10,604,582 | B2 | 3/2020 | Dimitrov et al. |
| 2010/0143245 | A1 | 6/2010 | Cheung |
| 2013/0078234 | A1 | 3/2013 | Takahashi et al. |
| 2017/0240637 | A1 | 8/2017 | Cheung et al. |
| 2019/0127471 | A1 | 5/2019 | Loo et al. |
| 2020/0031934 | A1 | 1/2020 | Gu et al. |

FOREIGN PATENT DOCUMENTS

| | | | |
|---|---|---|---|
| KR | 10-2013-0010117 | A | 1/2013 |
| KR | 10-2019-0015755 | A | 2/2019 |
| WO | 2011/109400 | A2 | 9/2011 |
| WO | 2017/214335 | A1 | 12/2017 |
| WO | 2018/177393 | A1 | 10/2018 |

OTHER PUBLICATIONS

Wall et al, Transgenic livestock: Progress and prospects for the future, 1996, Elsevier, p. 60-62 (Year: 1996).*
Meyskens et al, Cancer Prevention Obstacles Challenges and the Road Ahead, 2016, Oxford, vol. 108, p. 4-5 (Year: 2016).*
Borghaei et al., Immunotherapy of Cancer, 2009, European Journal of Pharmacology, entire document (Year: 2009).*
Loo et al, Clinical Cancer Research, 18, 14, 2012 (Year: 2012).*
Extended European Search Report, dated Dec. 14, 2022, for European Application No. 208377275-1111, 14 pages.
Japanese Office Action, mailed Sep. 27, 2022, for Japanese Application No. 2021-563149, 5 pages.
Nagashima et al., "B7—H3 Contributes to the Development of Pathogenic Th2 Cells in a Murine Model of Asthma," *J Immunol,* *181(6):* 4062-4071, 2008.
International Search Report and Written Opinion, dated Dec. 9, 2021, for International Application No. PCT/IB2021/000445. (12 pages).

(Continued)

*Primary Examiner* — Nelson B Moseley, II
*Assistant Examiner* — Josephine K Darpolor
(74) *Attorney, Agent, or Firm* — Seed Intellectual Property Law Group LLP

(57) ABSTRACT

Provided are an anti-B7-H3 antibody binding specifically to B7-H3 and a use thereof and, more particularly, are an anti-B7-H3 antibody or an antigen binding fragment thereof, a nucleic acid encoding the same, a vector carrying the nucleic acid, a cell transformed with the vector, a method for preparing the same, an antibody-drug conjugate or a multi-specific antibody comprising the same, and a pharmaceutical composition for preventing or treating cancer, autoimmune disease, or inflammatory disease, or a diagnostic composition, each composition comprising the same. The anti-B7-H3 antibody or antigen binding fragment thereof can bind to human and non-human B7-H3 at high affinity and can be endocytosized after binding thereto. Thus, the anti-B7-H3 antibody or antigen binding fragment thereof, or the antibody-drug conjugate or the multi-specific antibody comprising the same can be advantageously used for preventing, treating, or diagnosing cancer or tumor, autoimmune disease, or inflammatory disease.

15 Claims, 11 Drawing Sheets
Specification includes a Sequence Listing.

(56)                    References Cited

OTHER PUBLICATIONS

Loo et al., "Anti-B7—H3 antibody-drug conjugates as potential therapeutics for solid cancer," Presented at the 2016 American Associate for Cancer Research Annual Meeting: Abstract 1201, Jul. 15, 2016. (2 pages).

Park et al., "Aryl Sulfate is a Useful Motif for Conjugating and Releasing Phenolic Molecules: Sulfur Fluorine Exchange Click Chemistry Enables Discovery of Ortho-Hydroxy-Protected Aryl Sulfate Linker," *Bioconjugate Chem*. 30:1957-1968, Jun. 19, 2019. (12 pages).

Park et al., "Introduction of Para-Hydroxy Benzyl Spacer Greatly Expands the Utility of Ortho-Hydroxy-Protected Aryl Sulfate System: Application to Nonphenolic Payloads," *Bioconjugate Chem*. 30:1969-1978, Jun. 19, 2019. (10 pages).

Park et al., "Sulfonate Version of OHPAS Linker has Two Distinct Pathways of Breakdown: Elimination Route Allows Para-Hydroxy-Protected Benzylsulfonate (PHP-BS) to Serve as an Alternative Self-Immolative Group," *Bioconjugate Chem*. 31:1392-1399, Mar. 25, 2020. (8 pages).

International Search Report and Written Opinion, dated Oct. 20, 2020, for International Application No. PCT/KR2020/008928. (w/ English Translation of International Search Report) (16 pages).

GenBank, NCBI, Accession No. ADW08086.1, "immunoglobulin heavy chain variable region, partial [*Homo sapiens*]," Jul. 25, 2016. (2 pages).

GenBank, NCBI, Accession No. QDF61294.1, "immunoglobulin light chain variable region, partial [*Homo sapiens*]," Jul. 1, 2019. (1 page).

* cited by examiner

RE:reducing condition
12% SDS-PAGE

NR:non-reducing condition
8% SDS-PAGE

1: CD276-033E03
2: CD276-040F10
3: CD276-051H04
4: CD276-039C05
5: CD276-039C05_LS_001E10

6: CD276-039C05_LS_002A11
7: CD276-039C05_LS_002B07
8: CD276-039C05_LS_002C07
9: CD276-039C05_LS_002D03
10: CD276-039C05_LS_002H07

■ CD276-039C05

▨ CD276-040F10

Fab-ZAP conjugated antibody
Internalization-Cytotoxicity

Legend:
- ● CD276-033E03
- ⊟ CD276-039C05
- ▲ CD276-040F10
- ◆ CD276-051H04
- ◈ CD276-039C05_LS_002B07
- ⊖ CD276-039C05_LS_002D03
- ⊟ CD276-039C05_LS_002H07
- ▼ CD276-039C05_LS_001E10
- ◆ CD276-039C05_LS_002A11
- ⊖ CD276-039C05_LS_002C07
- ⊙ Saporin
- ✳ Fab-ZAP-IgG
- ✕ Control SAP

ANTIBODY BINDING SPECIFICALLY TO B7—H3 AND USE THEREOF

STATEMENT REGARDING SEQUENCE LISTING

The Sequence Listing associated with this application is provided in text format in lieu of a paper copy, and is hereby incorporated by reference into the specification. The name of the text file containing the Sequence Listing is 980136_401USPC_SEQUENCE_LISTING.txt. The text file is 34 KB, was created on May 10, 2022, and is being submitted electronically via EFS-Web.

TECHNICAL FIELD

The present invention relates to an anti-B7-H3 antibody binding specifically to B7-H3 and a use thereof and, more particularly, relates to an anti-B7-H3 antibody or an antigen binding fragment thereof, a nucleic acid encoding the same, a vector carrying the nucleic acid, a cell transformed with the vector, a method for preparing the antibody or antigen binding fragment thereof, an antibody-drug conjugate or a multi-specific antibody comprising the antibody or antigen binding fragment thereof, and a pharmaceutical composition for preventing or treating cancer, an autoimmune disease, or an inflammatory disease, or a diagnostic composition, each composition comprising the same.

BACKGROUND

Our immune systems are being finely adjusted to effectively eliminate invading pathogens while maintaining resistance to self-antigens. Among them, T lymphocytes are the main cells (effector cells) that can eliminate tumor cells.

Immune checkpoints are co-signaling molecules that play a pivotal role in T lymphocyte activation and regulate TCR (T cell receptor) signaling to be either inhibitory or stimulatory (Immunological reviews 2017, 276:52-65).

As part of evading immune surveillance, some tumor cells express the ligand protein of the immune checkpoint responsible for suppression on the cell surface, thereby inhibiting the function of T lymphocytes and making changes in the tumor micro-environment, resulting in suppression of immunity. Representative examples of successful tumor immunotherapy are the inhibitory immune checkpoints CTLA-4 (cytotoxic T lymphocyte antigen-4) and PD-1 (programmed death-1), and the corresponding antigen-presenting cells and tumor cell ligands, the B7 family molecules B7.1 (CD80) and B7.2 (CD86), and a monoclonal antibody blocker against B7-H1/PD-L1 (programmed death-ligand-1) (N Engl J Med. 2011, 364(26): 2517-2526; N Engl J Med., 2012, 366 (26)2455-2465; and N Engl J Med. 2013, 369(2): 134-144).

B7-H3 (B7 Homologue 3, or CD276 (Cluster of Differentiation 276)) is a member of the B7 family, and has 20-30% structural homology with B7.1 (CD80), B7.2 (CD86), B7-H1 (PD-L1), B7-DC (PD-L2), B7-H2 (ICOSL), B7-H4 (B7S1, B7x, Vtcn1), B7-H5 (VISTA, GI24, Dies1, PD-1H), B7-H6 (NCR3LG1) and B7-H7 (HHLA2) (Blood 2013, 121(5): 734-744; and Molecular Cancer Therapeutics 2017, 16(7): 1203-1211), and is a phylogenetically conserved protein with diverse biological functions. It was first discovered and introduced as a costimulatory molecule ligand in 2001 (Nature Immunology 2001, 2(3): 269274). However, recent studies have re-examined the findings and revealed that when a conjugate is formed with a ligand for a certain immunosuppressive receptor expressed on activated T cells or NK cells, antigen receptor signaling can be negatively regulated (Eur J Immunol. 2009, 39 (7): 1754-1764 and more), and a binding partner has not yet been identified.

B7-H3 mRNA is found in various normal tissues, but the protein is rarely expressed. When an immune activation signal is given, protein expression is induced in monocytes, macrophages, or dendritic cells, but it is overexpressed in various solid carcinomas, and expression was observed in prostate cancer, ovarian cancer, breast cancer, colon cancer, renal cancer, non-small cell lung cancer, pancreatic cancer, head and neck cancer, melanoma, glioblastoma, neuroblastoma, and other tumors (for example, small round blue cell tumors of childhood). In human B7-H3, 4Ig-B7-H3 (IgV-IgC-IgV-IgC) is the predominant form, 2Ig-B7-H3 is found slightly, while in murine, 2Ig-B7-H3 is the predominant form. However, both forms show similar functions (Genome Biol. 2005, 6:233.1-233.7; PNAS 2008, 105 (30):10277-10278). 4Ig-B7-H3 can inhibit the anti-tumor action of natural killer cells (PNAS 2004, 101 (34): 12640-12645). B7-H3 inhibitory signal is presumed to be made through interaction with molecules involved in TCR signaling (NF-kB, AP-1, NFAT, etc.), and in animal experiments, it was observed to inhibit Th1 (helper T cell), Th2 or Th17 (J. Immunol. 2004, 173:2500-2506; Immunol. Rev. 2009, 229 (1):145-151).

B7-H3 protein expression is very limited in normal cells, but is significantly increased in primary and metastatic tumors as well as tumor vasculature, and is found in many cell types, including differentiated tumor cells, tumor initiating or cancer stem cells (Medicographia 2014, 36 (2): 285-292; and Cancer cell 2017, 31:501-515), whose expression is strongly correlated with poor prognosis in some tumor types.

Promising therapeutic efficacy has been obtained in the development process of various modified antibodies, including monoclonal antibodies against B7-H3, and clinical development is in progress (Medicographia 2014, 36 (2): 285-292).

Under this technical background, the present inventors have developed an anti-B7-H3 antibody that specifically binds with affinity to human B7-H3 as well as non-human (for example, cynomolgus monkey, mouse, rat, etc.) B7-H3, and found that this antibody can be endocytosized after binding the cell surface B7-H3, and thus can serve as a desired immuno-oncology agent or a therapeutic agent for autoimmune disease or inflammatory disease. Based on the above, the present inventors completed the present invention.

The above information described in the background section is only for improving the understanding of the background of the present invention, and it may not include information forming the prior art known to those of ordinary skill in the art to which the present invention belongs.

BRIEF SUMMARY OF INVENTION

An object of the present invention is to provide an anti-B7-H3 antibody binding specifically to B7-H3 or an antigen binding fragment thereof.

Another object of the present invention is to provide a nucleic acid encoding the antibody or antigen binding fragment thereof and a vector carrying the same.

Another object of the present invention is to provide a cell transformed with the vector and a method for preparing the antibody or antigen binding fragment thereof using the same.

Another object of the present invention is to provide a pharmaceutical composition for preventing or treating cancer or tumor, autoimmune disease, or inflammatory disease, comprising the antibody or antigen binding fragment thereof, and a method for treating the disease using the same.

Another object of the present invention is to provide an antibody-drug conjugate or a multi-specific antibody comprising the antibody or antigen binding fragment thereof.

Another object of the present invention is to provide a pharmaceutical composition for preventing or treating cancer or tumor, autoimmune disease, or inflammatory disease, comprising the antibody or antigen binding fragment thereof, the antibody-drug conjugate or the multi-specific antibody, and a method for treating the disease using the same.

Another object of the present invention is to provide a composition for diagnosing cancer or tumor, autoimmune disease, or inflammatory disease, comprising the antibody or antigen binding fragment thereof, the antibody-drug conjugate or the multi-specific antibody, and a method for diagnosing the disease using the same.

In order to achieve the above object, the present invention provides an anti-B7-H3 antibody or an antigen binding fragment thereof comprising a heavy chain CDR1 selected from the group consisting of SEQ ID NOs: 1, 7, 13 and 19, a heavy chain CDR2 selected from the group consisting of SEQ ID NOs: 2, 8, 14 and 20, a heavy chain CDR3 selected from the group consisting of SEQ ID NOs: 3, 9, 15 and 21, a light chain CDR1 selected from the group consisting of SEQ ID NOs: 4, 10, 16, 22, 24, 26, 28, 30, 33 and 35, a light chain CDR2 selected from the group consisting of SEQ ID NOs: 5, 11, 17 and 31, and a light chain CDR3 selected from the group consisting of SEQ ID NOs: 6, 12, 18, 23, 25, 27, 29, 32, 34 and 36.

In addition, the present invention provides a nucleic acid encoding the anti-B7-H3 antibody or antigen binding fragment thereof, a recombinant expression vector comprising the nucleic acid, and a cell transformed with the recombinant expression vector.

In addition, the present invention provides a method for preparing an anti-B7-H3 antibody or an antigen binding fragment thereof, the method comprising (i) culturing the transformed cell, and (ii) recovering an anti-B7-H3 antibody or an antigen binding fragment thereof from the resulting cell culture solution.

In addition, the present invention provides an antibody-drug conjugate (ADC) comprising the anti-B7-H3 antibody or antigen binding fragment thereof and a drug.

In addition, the present invention provides a multi-specific antibody comprising the anti-B7-H3 antibody or antigen binding fragment thereof.

In addition, the present invention provides a pharmaceutical composition for preventing or treating cancer or tumor, an autoimmune disease, or an inflammatory disease, comprising the anti-B7-H3 antibody or antigen binding fragment thereof, the antibody-drug conjugate or the multi-specific antibody as an active ingredient and a pharmaceutically acceptable additive, and a method for treating the disease using the same.

In addition, the present invention provides a composition for diagnosing cancer or tumor, an autoimmune disease, or an inflammatory disease, comprising the anti-B7-H3 antibody or antigen binding fragment thereof, the antibody-drug conjugate or the multi-specific antibody, and a method for diagnosing the disease using the same.

BRIEF DESCRIPTION OF DRAWINGS

FIG. 6a illustrates a result obtained by measuring the binding force of the CD276-033E03 antibody for each cell line, FIG. 6b illustrates a result obtained by measuring the binding force of the CD276-051H04 antibody for each cell line, FIG. 6c illustrates a result obtained by measuring the binding force of the CD276-039C05 and CD276-040F10 antibodies for each cell line, and FIG. 6d illustrates a result obtained by measuring the binding force of the six antibodies for each cell line.

FIG. 9a illustrates a result obtained by identifying the endocytosis of the selected B7-H3 antibodies over time, and FIG. 9b illustrates a result obtained by measuring the degree of endocytosis of the antibodies at 18 hours.

DETAILED DESCRIPTION OF INVENTION

Figure 1:
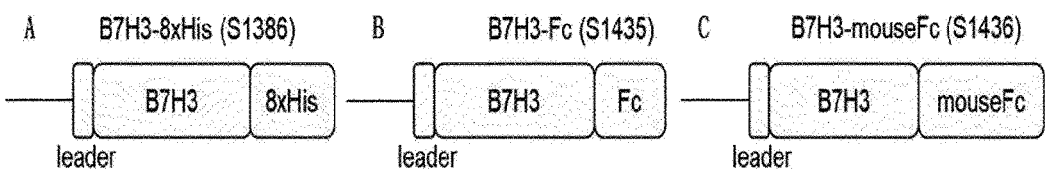
FIG. 1 illustrates a schematic diagram of a B7-H3 expression vector.

Unless defined otherwise, all technical and scientific terms used herein have the same meaning as commonly understood by those of ordinary skill in the art to which the present invention belongs. In general, the nomenclature used herein is one well known and commonly used in the art.

The B7-H3 protein, which acts as an antigen of the anti-B7-H3 antibody or antigen binding fragment thereof according to the present invention, is closely related to the inhibition of the activity of immune cells, and is a membrane protein present on the surface of immune cells, and acts as a co-inhibitory receptor of immune cells. The B7-H3 may be derived from mammals including primates such as humans and monkeys, and rodents such as mice and rats.

As used herein, the term "B7-H3" is a concept that collectively refers to any variant, isotype and species homologue of B7-H3, which is naturally expressed by cells. Preferably, it means a human B7-H3, but is not limited thereto, and may be a concept including B7-H3 of other mammals.

In the present invention, the anti-B7-H3 antibody or antigen binding fragment thereof preferably specifically binds to the amino acid sequence of the human B7-H3 protein represented by SEQ ID NO: 65 or a portion thereof, but is not limited thereto.

As used herein, the term "antibody" refers to an anti-B7-H3 antibody binding specifically to B7-H3. The scope of the present invention includes not only a complete antibody form binding specifically to B7-H3, but also an antigen binding fragment of the antibody molecule.

A complete antibody is a structure having two full-length light chains and two full-length heavy chains, each light chain connected to the heavy chain by a disulfide bond. A heavy chain constant region has gamma (γ), mu (μ), alpha (α), delta (δ) and epsilon (ε) types, and has subclasses gamma1 (γ1), gamma2 (γ2), gamma3 (γ3), gamma4 (γ4), alpha1 (α1) and alpha2 (α2). A light chain constant region has kappa (κ) and lambda (λ) types.

An "antigen binding fragment" or an "antibody fragment" of an antibody refers to a fragment having an antigen binding function, and may be in the form of Fab, F(ab'), F(ab')2 and Fv, etc. Among the antibody fragments, Fab has a structure having a variable region of a light chain and a heavy chain, a constant region of a light chain, and a first constant region (CH1) of a heavy chain, and has one antigen binding site. Fab' differs from Fab in that it has a hinge region comprising one or more cysteine residues at the C-terminus of the heavy chain CH1 domain. The F(ab')2 antibody is produced by forming a disulfide bond between cysteine residues in the hinge region of two Fab's. Fv refers to the smallest antibody fragment having only a heavy chain variable region and a light chain variable region.

In a double chain Fv (two-chain Fv), a heavy chain variable region and a light chain variable region are connected by a non-covalent bond, and single-chain Fv (scFv) may generally have a structure like a dimer like a double chain Fv in which a variable region of a heavy chain and a variable region of a light chain are connected by a covalent bond through a peptide linker or directly connected at the C-terminus. Such antibody fragments can be obtained using proteolytic enzymes (for example, papain-restricted digestion of the whole antibody yields Fab, pepsin digestion yields F(ab')2 fragments), and can also be constructed through gene recombination technology.

In one embodiment, the antibody according to the present invention is in the form of an Fv (for example, scFv) or in the form of a complete antibody. In addition, a heavy chain constant region may be any one isotype of gamma (γ), mu (μ), alpha (α), delta (δ) or epsilon (ε). For example, a constant region is gamma1 (IgG1), gamma 3 (IgG3) or gamma 4 (IgG4). A light chain constant region may be a kappa or lambda type.

The antibody of the present invention includes a monoclonal antibody, a multi-specific antibody, a human antibody, a humanized antibody, a chimeric antibody, a single-chain Fv (scFV), a single-chain antibody, a Fab fragment, a F(ab') fragment, a disulfide-linked Fv (sdFV) and an anti-idiotypic (anti-Id) antibody, or an epitope-binding fragment of such antibodies, and the like, but is not limited thereto. For example, the antibody of the present invention may be a human antibody sequence in which all of the amino acid sequences constituting the antibody are composed of human immunoglobulin sequences, and if necessary, may be modified into various forms such as a humanized antibody, a chimeric antibody, etc. according to methods well known in the art.

As used herein, an "antibody variable domain" refers to light chain and heavy chain portions of an antibody molecule comprising an amino acid sequence of a complementarity determining region (CDR) and a framework region (FR). VH refers to a variable domain of a heavy chain. VL refers to a variable domain of a light chain.

A "complementarity determining region" (CDR; i.e., CDR1, CDR2, and CDR3) refers to the amino acid residues of antibody variable domains that are required for antigen binding. Each variable domain typically has three CDR regions identified as CDR1, CDR2 and CDR3.

The present invention provides an anti-B7-H3 antibody or an antigen binding fragment thereof comprising a heavy chain CDR1 selected from the group consisting of SEQ ID NOs: 1, 7, 13 and 19, a heavy chain CDR2 selected from the group consisting of SEQ ID NOs: 2, 8, 14 and 20, a heavy chain CDR3 selected from the group consisting of SEQ ID NOs: 3, 9, 15 and 21, a light chain CDR1 selected from the group consisting of SEQ ID NOs: 4, 10, 16, 22, 24, 26, 28, 30, 33 and 35, a light chain CDR2 selected from the group consisting of SEQ ID NOs: 5, 11, 17 and 31, and a light chain CDR3 selected from the group consisting of SEQ ID NOs: 6, 12, 18, 23, 25, 27, 29, 32, 34 and 36.

Specifically, the anti-B7-H3 antibody or antigen binding fragment thereof of the present invention comprises:

a heavy chain CDR1 of SEQ ID NO: 1, a heavy chain CDR2 of SEQ ID NO: 2, a heavy chain CDR3 of SEQ ID NO: 3, a light chain CDR1 of SEQ ID NO: 4, a light chain CDR2 of SEQ ID NO: 5, and a light chain CDR3 of SEQ ID NO: 6;

a heavy chain CDR1 of SEQ ID NO: 7, a heavy chain CDR2 of SEQ ID NO: 8, a heavy chain CDR3 of SEQ ID NO: 9, a light chain CDR1 of SEQ ID NO: 10, a light chain CDR2 of SEQ ID NO: 11, and a light chain CDR3 of SEQ ID NO: 12;

a heavy chain CDR1 of SEQ ID NO: 13, a heavy chain CDR2 of SEQ ID NO: 14, a heavy chain CDR3 of SEQ ID NO: 15, a light chain CDR1 of SEQ ID NO: 16, a light chain CDR2 of SEQ ID NO: 17, and a light chain CDR3 of SEQ ID NO: 18;

a heavy chain CDR1 of SEQ ID NO: 19, a heavy chain CDR2 of SEQ ID NO: 20, a heavy chain CDR3 of SEQ ID NO: 21, a light chain CDR1 of SEQ ID NO: 22, a light chain CDR2 of SEQ ID NO: 11, and a light chain CDR3 of SEQ ID NO: 23;

a heavy chain CDR1 of SEQ ID NO: 19, a heavy chain CDR2 of SEQ ID NO: 20, a heavy chain CDR3 of SEQ ID NO: 21, a light chain CDR1 of SEQ ID NO: 24, a light chain CDR2 of SEQ ID NO: 11, and a light chain CDR3 of SEQ ID NO: 25;

a heavy chain CDR1 of SEQ ID NO: 19, a heavy chain CDR2 of SEQ ID NO: 20, a heavy chain CDR3 of SEQ ID NO: 21, a light chain CDR1 of SEQ ID NO: 26, a light chain CDR2 of SEQ ID NO: 11, and a light chain CDR3 of SEQ ID NO: 27;

a heavy chain CDR1 of SEQ ID NO: 19, a heavy chain CDR2 of SEQ ID NO: 20, a heavy chain CDR3 of SEQ ID NO: 21, a light chain CDR1 of SEQ ID NO: 28, a light chain CDR2 of SEQ ID NO: 5, and a light chain CDR3 of SEQ ID NO: 29;

a heavy chain CDR1 of SEQ ID NO: 19, a heavy chain CDR2 of SEQ ID NO: 20, a heavy chain CDR3 of SEQ ID NO: 21, a light chain CDR1 of SEQ ID NO: 30, a light chain CDR2 of SEQ ID NO: 31, and a light chain CDR3 of SEQ ID NO: 32;

a heavy chain CDR1 of SEQ ID NO: 19, a heavy chain CDR2 of SEQ ID NO: 20, a heavy chain CDR3 of SEQ ID NO: 21, a light chain CDR1 of SEQ ID NO: 33, a light chain CDR2 of SEQ ID NO: 11, and a light chain CDR3 of SEQ ID NO: 34; or a heavy chain CDR1 of SEQ ID NO: 19, a heavy chain CDR2 of SEQ ID NO: 20, a heavy chain CDR3 of SEQ ID NO: 21, a light chain CDR1 of SEQ ID NO: 35, a light chain CDR2 of SEQ ID NO: 11, and a light chain CDR3 of SEQ ID NO: 36.

In addition, the anti-B7-H3 antibody or antigen binding fragment thereof of the present invention may comprise a heavy chain variable region of SEQ ID NO: 37, 39, 41 or 43, or may comprise a light chain variable region of SEQ ID NO: 38, 40, 42, 44, 45, 46, 47, 48, 49 or 50.

Specifically, it may comprise a heavy chain variable region of SEQ ID NO: 37 and a light chain variable region of SEQ ID NO: 38; a heavy chain variable region of SEQ ID NO: 39 and a light chain variable region of SEQ ID NO: 40; a heavy chain variable region of SEQ ID NO: 41 and a light chain variable region of SEQ ID NO: 42; a heavy chain variable region of SEQ ID NO: 43 and a light chain variable region of SEQ ID NO: 44; a heavy chain variable region of SEQ ID NO: 43 and a light chain variable region of SEQ ID NO: 45; a heavy chain variable region of SEQ ID NO: 43 and a light chain variable region of SEQ ID NO: 46; a heavy chain variable region of SEQ ID NO: 43 and a light chain variable region of SEQ ID NO: 47; a heavy chain variable region of SEQ ID NO: 43 and a light chain variable region of SEQ ID NO: 48; a heavy chain variable region of SEQ ID NO: 43 and a light chain variable region of SEQ ID NO: 49; or a heavy chain variable region of SEQ ID NO: 43 and a light chain variable region of SEQ ID NO: 50.

"Framework region" (FR) is a variable domain residue other than a CDR residue. Each variable domain typically has four FRs identified as FR1, FR2, FR3 and FR4.

The antibody is monovalent or bivalent, and includes a single-chain or a double chain. Functionally, the binding affinity $(K_D)$ of the antibody is in the range of $10^{-8}$M to $10^{-12}$M. For example, the binding affinity of the antibody is $10^{-8}$ M to $10^{-12}$ M, $10^{-9}$ M to $10^{-12}$ M, $10^{-10}$ M to $10^{-12}$ M, $10^{-8}$ M to $10^{-11}$ M, $10^{-9}$ M to $10^{-11}$ M, $10^{-10}$ M to $10^{--11}$ M, $10^{-8}$ M to $10^{-10}$ M, $10^{-9}$ M to $10^{-10}$ M, or $10^{-8}$ M to $10^{-9}$ M.

"Phage display" is a technique for displaying a variant polypeptide as a fusion protein with at least a portion of an envelope protein on the surface of a phage, for example a filamentous phage particle. The usefulness of phage display lies in the fact that it can rapidly and efficiently sort sequences that bind to a target antigen with high affinity by targeting a large library of randomized protein variants. Displaying peptide and protein libraries on phage has been used to screen millions of polypeptides for identifying polypeptides with specific binding properties.

The phage display technology has the advantage of being able to generate a large antibody library with various sequences in a short time compared to conventional hybridoma and recombination methods for producing antibodies with desired characteristics. In addition, since no immunity is required, the phage antibody library can also generate antibodies against antigens that are toxic or of low antigenicity. The phage antibody library can also be used to generate and identify novel therapeutic antibodies.

A technology capable of identifying and isolating high affinity antibodies from a phage display library is important for isolating novel therapeutic antibodies. Isolation of high affinity antibodies from a library may depend on the size of the library, production efficiency in bacterial cells, and diversity of the library.

The anti-B7-H3 antibody or antigen binding fragment thereof of the present invention includes an antibody or an antigen binding fragment thereof in which a part of the amino acid sequence is substituted through conservative substitution in the anti-B7-H3 antibody or antigen binding fragment thereof according to the present invention.

As used herein, "conservative substitution" refers to a modification of a polypeptide including substituting one or more amino acids with amino acids having similar biochemical properties that do not cause loss of biological or biochemical functions of the polypeptide. A "conservative amino acid substitution" is a substitution in which an amino acid residue is replaced by an amino acid residue having a similar side chain. Classes of amino acid residues having similar side chains have been defined in the art and are well known. These classes are amino acids with basic side chains (for example, lysine, arginine, histidine), amino acids with acidic side chains (for example, aspartic acid, glutamic acid), amino acids with uncharged polar side chains (for example, glycine, asparagine, glutamine, serine, threonine, tyrosine, cysteine), amino acids with non-polar side chains (for example, alanine, valine, leucine, isoleucine, proline, phenylalanine, methionine, tryptophan), amino acids with beta-branched side chains (for example, threonine, valine, isoleucine) and amino acids with aromatic side chains (for example, tyrosine, phenylalanine, tryptophan, histidine). The antibody of the present invention may still retain an activity even with such conservative amino acid substitutions as described above.

In addition, the present invention provides a nucleic acid encoding the anti-B7-H3 antibody or antigen binding fragment thereof according to the present invention. A nucleic acid as used herein may be present in cells or cell lysates, or may also exist in a partially purified form or a substantially pure form. A nucleic acid is "isolated" or "substantially pure" when it has been purified from other cellular components or other contaminants, for example, nucleic acids or proteins of other cells by standard techniques including alkali/SDS treatment, CsCl banding, column chromatography, agarose gel electrophoresis, and others well known in the art. The nucleic acid of the present invention may be, for example, DNA or RNA, and may or may not contain an intron sequence. Nucleotides, which are the basic building blocks of nucleic acids, include not only natural nucleotides, but also analogues in which sugar or base regions are modified. The sequence of the nucleic acid encoding heavy chain and light chain variable regions of the present invention may be modified. Such modifications include additions, deletions, or non-conservative or conservative substitutions of nucleotides.

In the present invention, a nucleic acid encoding the anti-B7-H3 antibody may comprise any one or more sequences selected from the group consisting of the polynucleotides of SEQ ID NOs: 51, 53, 55, and 57 encoding a heavy chain variable region, and the polynucleotides of SEQ ID NOs: 52, 54, 56, and 58 to 64 encoding a light chain variable region.

Considering the modifications having the above-described biological equivalent activity, it is construed that the antibody of the present invention or a nucleic acid molecule encoding the same includes a sequence exhibiting substantial identity to the sequence set forth in SEQ ID NO. The substantial identity refers to a sequence exhibiting at least 90% homology, preferably at least 95% homology, more preferably at least 96%, at least 97%, at least 98%, or at least 99% homology, when the sequence of the present invention and any other sequences are arranged to correspond to the maximum, and the aligned sequence is analyzed using an algorithm commonly used in the art.

Such homology may be determined by sequence comparison and/or alignment by methods known in the art. For example, the sequence homology of the nucleic acid or protein of the present invention may be determined using a sequence comparison algorithm (for example, NCBI Basic Local Alignment Search Tool; BLAST), manual alignment, visual inspection, and the like.

In another aspect, the present invention relates to a recombinant expression vector comprising the nucleic acid. For the expression of the anti-B7-H3 antibody or antigen binding fragment thereof according to the present invention, DNA encoding partial or full-length light and heavy chains may be obtained by standard molecular biology techniques (for example, PCR amplification or cDNA cloning using a hybridoma expressing a target antibody), and the DNA may be "operably linked" to transcriptional and translational control sequences and inserted into an expression vector. Vector components generally include, but are not limited to, one or more of the following: a signal sequence, an origin of replication, one or more marker genes, an enhancer element, a promoter, and a transcription termination sequence.

As used herein, the term "vector" refers to a means for expressing a target gene in a host cell, including a plasmid vector; a cosmid vector; a viral vector such as a bacteriophage vector, an adenoviral vector, a retroviral vector and an adeno-associated viral vector, and the like. In the vector, a nucleic acid encoding an antibody or an antigen binding fragment thereof is operably linked to a promoter.

As used herein, the term "operably linked" refers to the ligation of a gene encoding an antibody or an antigen binding fragment thereof into a vector such that transcriptional and translational control sequences in the vector serve the intended function of regulating the transcription and translation of the antibody gene. Expression vectors and expression control sequences are selected to be compatible with the cells for expression used. A light chain gene and a heavy chain gene of an antibody are inserted into separate vectors, or both genes are inserted into the same expression vector. The antibody gene is inserted into the expression vector by standard methods (for example, ligation of the complementary restriction enzyme sites on the antibody gene fragment and vector, or blunt end ligation if no restriction enzyme sites are present).

In some cases, the recombinant expression vector may comprise a sequence encoding a signal peptide that facilitates secretion of the antibody chain from the transformed cell. The antibody chain gene and signal peptide-coding sequence may be cloned into a vector in frame so that the signal peptide is expressed by binding to the amino terminus of the antibody chain. The signal peptide may be an immunoglobulin signal peptide or a heterologous signal peptide (i.e., a signal peptide derived from a protein other than immunoglobulin). In addition, the recombinant expression vector may include a regulatory sequence for controlling the expression of the antibody chain gene in the transformed cell. A "regulatory sequence" may include a promoter, an enhancer and other expression control elements (for example, a polyadenylation signal) that control the transcription or translation of the antibody chain gene. Those of ordinary skill in the art can recognize that the design of the expression vector may vary by selecting different regulatory sequences depending on factors such as the selection of cells to be transformed, the level of protein expression, and the like.

In addition, the vector of the present invention may comprise other sequences to be fused to the antibody gene in order to facilitate purification of the antibody expressed from the vector. This sequence may be, for example, a gene such as glutathione S-transferase (Pharmacia, USA), maltose binding protein (NEB, USA), FLAG (IBI, USA), 6× His (hexahistidine; Quiagen, USA), and the like.

The vector includes an antibiotic resistance gene commonly used in the art as a selection label, and this gene includes, for example, a gene for resistance to ampicillin, gentamicin, carbenicillin, chloramphenicol, streptomycin, kanamycin, geneticin, neomycin and tetracycline.

In addition, the present invention provides a cell transformed with the recombinant expression vector. The cell according to the present invention may be an animal cell, a plant cell, yeast, *E. coli* and an insect cell, etc., but is not limited thereto.

Specifically, the cell according to the present invention may be a prokaryotic cell such as *E. coli, Bacillus subtilis, Streptomyces* sp., *Pseudomonas* sp., *Proteus mirabilis* or *Staphylococcus* sp. In addition, the cell may be a fungi such as *Aspergillus* sp., a lower eukaryotic cell such as *Pichia pastoris, Saccharomyces cerevisiae, Schizosaccharomyces* sp. and *Neurospora crassa,* and a eukaryotic cell such as a cell of a higher eukaryote (for example, an insect).

In addition, the cell according to the present invention may be derived from a plant or a mammal. For example, COS-7 (monkey kidney cells 7) cells, BHK (baby hamster kidney) cells, CHO (Chinese hamster ovary) cells, CHOK1 cells, DXB-11 cells, DG-44 cells, CHO/-DHFR cells, CV1 cells, HEK293 cells, BHK cells, TM4 cells, VERO cells, HELA cells, MDCK cells, BRL 3A cells, W138 cells, Hep G2 cells, SK-Hep cells, MMT cells, TRI cells, MRC 5 cells, FS4 cells, 3T3 cells, RIN cells, A549 cells, PC12 cells, K562 cells, PER.C6 cells, SP2/0 cells, NS0 cells, U20S cells, or HT1080 cells, etc., may be available, but are not limited thereto. Preferably, COS7 cells, NS0 cells, SP2/0 cells, CHO cells, W138 cells, BHK cells, MDCK cells, myeloma cell line, HuT 78 cells and HEK293 cells, more preferably CHO cells may be used.

Various cell/vector combinations may be used to express the anti-B7-H3 antibody according to the present invention. Specifically, expression vectors suitable for eukaryotic cells include expression vectors derived from SV40, bovine papillomavirus, adenovirus, adeno-associated virus, cytomegalovirus and retrovirus, but are not limited thereto. Expression vectors that may be used for bacterial cells include *E. coli*-derived bacterial plasmids such as pET, pRSET, pBluescript, pGEX2T, pUC, col E1, pCR1, pBR322, pMB9 and derivatives thereof; plasmids with a wider host range, such as RP4; phage DNA, such as various phage lambda derivatives such as λgt10, λgt11, and NM989; and other DNA phages such as M13 and filamentous single-stranded DNA phages. An expression vector that is useful for yeast cells is YEp plasmid and a derivative thereof. A vector that is useful for insect cells is pVL941.

The vector is transduced or transfected into cells. A number of different techniques commonly used to introduce exogenous nucleic acid (DNA or RNA) into prokaryotic or eukaryotic cells for "transduction" or "transfection," for example, electrophoresis, calcium phosphate precipitation, DEAE-dextran transfection or lipofection, and the like can be used.

In addition, the present invention provides a method for preparing the antibody or antigen binding fragment thereof, the method comprising: (i) culturing the transformed cell; and (ii) recovering an anti-B7-H3 antibody or an antigen binding fragment thereof from the resulting cell culture solution. When a recombinant expression vector capable of expressing the anti-B7-H3 antibody or antigen binding fragment thereof is introduced into a mammalian cell, the antibody or antigen binding fragment thereof may be prepared by culturing the cells for a period of time sufficient to allow the antibody to be expressed in the cell, or more preferably, for a period of time sufficient to allow the antibody to be secreted into the culture medium in which the cell is cultured.

The cells may be cultured in various media, and commercially available media may be used without limitation as the culture media. All other essential supplements known to those of ordinary skill in the art may be included in appropriate concentrations. Suitable culture conditions, for example, temperature, pH, etc., have already been used for protein expression in the selected host cell, and will be apparent to those of ordinary skill in the art.

In some cases, the expressed antibody can be isolated from the cell culture solution and purified uniformly. Isolation or purification of the antibody may be performed by a conventional protein isolation and purification method, for example chromatography. The chromatography may include, for example, affinity chromatography using a protein A column or a protein G column, ion exchange chromatography, hydrophobic chromatography, or hydroxylapatite chromatography. In addition to the above chromatography, the antibody may be isolated and purified by further combining filtration, ultrafiltration, salting out, dialysis, and the like.

In addition, the present invention provides an antibody-drug conjugate comprising the antibody or antigen binding fragment thereof and a drug.

In the antibody-drug conjugate, the anticancer drug must be stably bound to the antibody until the anticancer drug is delivered to the target cancer cell. The drug delivered to the target must be released from the antibody to induce the death of the target cell. To this end, when the drug is stably bound to the antibody and released from the target cell, it must have sufficient cytotoxicity to induce the death of the target cell.

The drug is an agent that exhibits a pharmacological effect, and refers to a compound that may be bound to the antibody or antigen binding fragment thereof of the present invention, may be isolated from the antibody or antigen binding fragment thereof by acidic conditions, and may exhibit a therapeutic effect on the target cell. The drug may include a cytotoxin, a radioactive isotope, an antiproliferative agent, a pro-apoptotic agent, a chemotherapeutic agent, and a therapeutic nucleic acid, but is not limited thereto.

The antibody-drug conjugate may be internalized into the cell and mediate antibody-dependent cytotoxicity.

As used herein, the term "cytotoxic activity" refers to an effect of an antibody-drug conjugate or an antibody-drug conjugate of killing cells of metabolite in the cells, inhibiting cell proliferation, or inhibiting growth. Cytotoxic activity may be expressed as the IC50 value, which is the concentration (molar or mass) per unit volume at which one-half of the cells survive.

The term "cytotoxin" generally refers to an agent that inhibits or prevents the function of a cell and/or destroys a cell. Representative cytotoxins include antibiotics, tubulin polymerization inhibitors, alkylating agents that bind to and destroy DNA, and agents that destroy the function or protein synthesis of essential cellular proteins such as protein kinases, phosphatases, topoisomerases, enzymes and cyclins. Examples of cytotoxins include taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol and puromycin, and analogues or homologues thereof, but are not limited thereto.

For radiotherapy application, the antibody of the present invention may comprise a high energy radioactive isotope. The isotope may be bound directly to the antibody, for example at a cysteine residue present in the antibody, or may mediate binding of the antibody to the radioactive isotope using a chelate. The radioactive isotope suitable for radiotherapy includes an α-emitter, a β-emitter, and an Auger electron, but is not limited thereto. The radioactive isotope useful for diagnostic application includes a positron emitter and a γ-emitter.

An antiproliferative agent and a pro-apoptotic agent include PPAR-gamma (for example, cyclopentenone prostaglandins (cyPGs)), retinoids, triterpenoids (for example, cycloartane, lupan, uric acid, oleanane, preedelan, dammarane, cucurbitacin and limonoid triterpenoids), EGF receptor inhibitors (for example, HER4), rapamycin, CALCITRIOL (1,25-dihydroxycholecalciferol (vitamin D)), aromatase inhibitors (FEMARA (retrozone)), telomerase inhibitors, iron chelating agents (for example, 3-aminopyridine-2-carboxaldehyde thiosemicarbazone (triapine)), apoptin (virus protein 3-VP3 from chicken anemia virus), Bcl-2 and Bcl-X (L) inhibitors, TNF-alpha, FAS ligand, TNF-related apoptosis-inducing ligand (TRAIL/Apo2L), TNF-alpha/FAS ligand/TNF-related apoptosis-inducing ligand (TRAIL/Apo2L) signaling activators, and PI3K-Akt survival pathway signaling inhibitors (for example, UCN-01 and geldanamycin).

A "chemotherapeutic agent" is a chemical compound useful in the treatment of cancer, regardless of its mechanism of action. Classes of chemotherapeutic agents include alkylating agents, antimetabolites, spindle toxic plant alkaloids, cytotoxic/anti-tumor antibiotics, topoisomerase inhibitors, antibodies, photosensitizers, and kinase inhibitors, but are not limited thereto. A chemotherapeutic agent includes a compound used in "targeted therapy" and traditional chemotherapy.

The conjugate can be constructed by a known method by binding a drug to an antibody or an antigen binding fragment thereof. The antibody and the drug may be directly bound through their own linking group, and the like, or may be indirectly bound through a linker or other substances. The main mechanisms by which the drug is cleaved from the antibody include hydrolysis at acidic pH of lysosomes (hydrazone, acetal and cis-aconitate-like amides), peptide cleavage by lysosomal enzymes (cathepsin and other lysosomal enzymes), and the reduction of disulfide. As a result of these various cleavage mechanisms, the mechanisms by which the drug is linked to the antibody vary widely and any suitable linker may be used.

Suitable linking groups for binding an antibody to a drug are well known in the art and include, for example, a disulfide group, a thioether group, an acid-cleavable group, a photo-cleavable group, a peptidase-cleavable group, and an esterase-cleavable group.

When the drug is directly bound, the linking group may include, for example, a disulfide bond using an SH group or a bond mediated by maleimide. For example, an intramolecular disulfide bond of the antibody Fc region and a disulfide bond of the drug are reduced, and both are linked by a disulfide bond. In addition, it includes a method through a maleimide and a method for genetically introducing cysteine into the antibody.

An antibody and a drug may be indirectly linked through other substances (linkers). The linker preferably has one or two or more functional groups that react with an antibody, a drug, or both. Examples of the functional group include an amino group, a carboxyl group, a mercapto group, a maleimide group, a pyridinyl group, and the like.

In addition, the present invention provides a multi-specific antibody comprising the antibody or antigen binding fragment thereof. The multi-specific antibody refers to an antibody capable of binding to two or more different types of antigens (target proteins), and is a form prepared by genetic engineering or any method. The multi-specific antibody includes a bi-specific antibody, a tri-specific antibody or a tetra-specific antibody.

The multi-specific antibody is preferably in a form in which the anti-B7-H3 antibody according to the present invention is bound to an antibody or a fragment thereof having the binding ability to an immune effector cell-specific target molecule. The immune effector cell-specific target molecule is preferably selected from TCR/CD3, CD16 (FcγRIIIa) CD44, CD56, CD69, CD64 (FcγRT), CD89 and CD11b/CD18 (CR3), but is not limited thereto.

The multi-specific antibody is preferably in a form in which the anti-B7-H3 antibody according to the present invention is bound to an antibody or a fragment thereof having the binding ability to a cytokine that stimulates or inhibits immunity. A cytokine that stimulates or inhibits immunity is preferably selected from, for example, IL-2, IL-6, IL-7, IFNα, GM-CSF, IL-10, and TGF-β, but is not limited thereto.

The multi-specific antibody is preferably in a form in which the anti-B7-H3 antibody according to the present invention is bound to an antibody or a fragment thereof having the binding ability to a target used for cancer treatment, for example, PD-1, PD-L1, VEGF, EGFR, Her2/neu, VEGF receptor, other growth factor receptors, CD20, CD40, CTLA-4, TIGIT, TIM-3, LAG-3, OX-40, 4-IBB and ICOS, but is not limited thereto.

Antibodies belonging to a multi-specific antibody may be classified into scFv-based antibodies, Fab-based antibodies, and IgG-based antibodies, etc. In the case of a bi-specific antibody, since it can inhibit or amplify two signals at the same time, it may be more effective than the case of inhibiting/amplifying one signal. Compared with the case where each signal is treated with each signal inhibitor, it is possible to administer a low dose and inhibit/amplify two signals in the same time and space.

Methods for preparing bi-specific antibodies are well known. Traditionally, recombination production of bispecific antibodies is based on the co-expression of two immunoglobulin heavy chain/light chain pairs under conditions in which the two heavy chains have different specificities.

In the case of a bi-specific antibody based on an scFv, a hybrid scFv can be prepared in the form of a heterodimer by combining the VL and VH of different scFvs with each other to make a diabody, and different scFvs can be linked to each other to make a tandem ScFv, and a heterodimeric miniantibody can be prepared by expressing CH1 and CL of the Fab at the ends of each scFv, and a heterodimeric scFv-type minibody can be prepared by substituting some amino acids of the CH3 domain, which is the homodimeric domain of Fc, to change to a heterodimer structure in the 'knob into hole' form, and expressing these altered CH3 domains at different scFv ends.

In the case of a bi-specific antibody based on a Fab, a heterodimeric Fab can be prepared by combining individual Fab's directed against a specific antigen with each other using a disulfide bond or a mediator, and the antigen valency can be doubled by expressing scFvs for different antigens at the ends of the heavy or light chains of a specific Fab, or it can be prepared to have four antigen valencies in the form of homodimers by providing a hinge region between the Fab and scFv. In addition, a dual-targeted bibody with three antigen valency can be prepared by fusing scFvs for different antigens to the light and heavy chain ends of the Fab, and a triple-targeted bibody with three antigen valency can be prepared by fusing different scFvs to the light and heavy chain ends of the Fab, and it can also be obtained by chemically conjugating three different Fabs.

In the case of a bi-specific antibody based on an IgG, a method for producing a bi-specific antibody by re-crossing a mouse and a rat hybridoma to produce a hybrid hybridoma (also known as quadromas) is known. In addition, it is also possible to prepare a bi-specific antibody in the so-called 'Holes and Knob' form, which is made in the form of a heterodimer by modifying some amino acids of the CH3 homodimeric domain of Fc with respect to different chains while sharing the light chain portion. (scFv)4-IgG in a homodimeric form can also be prepared by fusion-expressing two different scFvs in constant domains instead of the variable domains of the light and heavy chains of IgG.

In addition, the present invention provides a pharmaceutical composition for preventing or treating cancer or tumor, autoimmune disease, or inflammatory disease, comprising the anti-B7-H3 antibody or antigen binding fragment thereof, or the multi-specific antibody or the antibody-drug conjugate comprising the same as an active ingredient, and a pharmaceutically acceptable additive.

The cancer or tumor, autoimmune disease, or inflammatory disease may be related to the expression or overexpression of B7-H3.

In the present invention, "cancer" and "tumor" are used in substantially the same sense, and refer to or mean a physiological condition in mammals that is typically characterized by unregulated cell growth and proliferation.

"Prevention" refers to any act of inhibiting or delaying the progression of cancer or tumor, autoimmune disease, or inflammatory disease by administration of the composition according to the present invention, and "treatment" refers to inhibiting the development of cancer or tumor, alleviating or eliminating cancer or tumor, inhibiting, alleviating or eliminating autoimmune disease or inflammatory disease.

Cancer or carcinoma that can be treated with the composition of the present invention is not particularly limited, and includes both solid cancer and hematological cancer. Examples of such cancer may be selected from the group consisting of skin cancer such as melanoma, liver cancer, hepatocellular carcinoma, stomach cancer, breast cancer, lung cancer, ovarian cancer, bronchial cancer, nasopharyngeal cancer, laryngeal cancer, pancreatic cancer, bladder cancer, colorectal cancer, colon cancer, pancreatic cancer, cervical cancer, brain cancer, prostate cancer, non-small cell lung cancer, bone cancer, skin cancer, thyroid cancer, parathyroid cancer, renal cancer, esophageal cancer, biliary tract cancer, testicular cancer, rectal cancer, head and neck cancer, cervical spine cancer, ureter cancer, osteosarcoma, neuroblastoma, fibrosarcoma, rhabdomyosarcoma, astrocytoma, glioblastoma, neuroblastoma, glioma, and other tumors (for example, small round blue cell tumors of childhood), but are not limited thereto.

More preferably, the cancer or tumor may be characterized in that the B7-H3 protein is expressed, and may be characterized by being selected from the group consisting of prostate cancer, ovarian cancer, breast cancer, colon cancer, renal cancer, non-small cell lung cancer, pancreatic cancer, head and neck cancer, melanoma, glioblastoma, neuroblastoma and other tumors (for example, small round blue cell tumors of childhood). The cancer may be a primary cancer or a metastatic cancer.

In the present invention, the autoimmune disease or inflammatory disease may be asthma, rheumatoid arthritis, or multiple sclerosis, but is not limited thereto.

In the present invention, the pharmaceutical composition comprises a therapeutically effective amount of an anti-B7-H3 antibody or an antigen binding fragment thereof together with a pharmaceutically acceptable additive. A "pharmaceutically acceptable additive" is a substance that can be added to an active ingredient to help formulate or stabilize a pharmaceutical composition, and does not cause significant toxic effects to the patient.

The additive refers to a carrier or diluent that does not irritate the patient and does not inhibit the biological activity and property of the administered compound. Pharmaceutical carriers acceptable for compositions formulated as liquid solutions are sterile and biocompatible, and saline, sterile water, Ringer's solution, buffered saline, albumin injection solution, dextrose solution, maltodextrin solution, glycerol, ethanol, and a mixture thereof may be used, and other conventional additives such as antioxidants, buffers, and bacteriostats may be added as needed. In addition, it may be formulated in the form of an injectable formulation such as an aqueous solution, suspension, emulsion, etc., pills, capsules, granules or tablets by additionally adding diluents, dispersants, surfactants, binding agents and lubricants.

A pharmaceutically acceptable carrier includes sterile aqueous solutions or dispersions and sterile powders for the preparation of sterile injectable solutions or dispersions for extemporaneous administration. The composition is preferably formulated for parenteral injection. The composition may be formulated as solutions, microemulsions, liposomes, or other customized formulations suitable for high drug concentrations. The carrier may be a solvent or dispersion medium containing, for example, water, ethanol, a polyol (for example, glycerol, propylene glycol and liquid polyethylene glycol, etc.) and suitable mixtures thereof. In some cases, isotonic agents, for example, sugars, polyalcohols such as mannitol, sorbitol or sodium chloride may be included in the composition. Each formulation may be prepared using methods well known in the pharmaceutical art.

The dosage of the pharmaceutical composition according to the present invention is not particularly limited, but may vary depending on various factors including the health condition and body weight of the patient, the severity of the disease, the type of drug, the route of administration, and the time of administration. The pharmaceutical composition according to the present invention may be administered in one dose or multiple doses per day through various routes of oral or parenteral routes typically accepted into mammals including humans, rats, mice, livestock, and the like. Specifically, it may be administered in a conventional manner via oral, intrarectal, topical, intravenous, intraperitoneal, intramuscular, intraarterial, transdermal, intranasal, inhalational, intraocular, intrapulmonary or intradermal routes, but is not limited thereto.

The pharmaceutical composition according to the present invention may be administered to a patient as a bolus or by continuous infusion, if necessary. For example, bolus administration of the antigen binding fragment of the anti-B7-H3 antibody of the present invention represented by a Fab fragment may be in an amount of 0.0025 to 100 mg/kg body weight, 0.025 to 0.25 mg/kg, 0.010 to 0.10 mg/kg, or 0.10 to 0.50 mg/kg. In the case of continuous infusion, the antigen binding fragment of the anti-B7-H3 antibody of the present invention represented by a Fab fragment may be administered in an amount of 0.001 to 100 mg/kg body weight/min, 0.0125 to 1.25 mg/kg/min, 0.010 to 0.75 mg/kg/min, 0.010 to 1.0 mg/kg/min or 0.10 to 0.50 mg/kg/min for a period of time of 1 hour to 24 hours, 1 hour to 12 hours, 2 hours to 12 hours, 6 hours to 12 hours, 2 hours to 8 hours, or 1 hour to 2 hours. When the anti-B7-H3 antibody or antigen binding fragment thereof of the present invention is administered, the dosage may be about 1 to 10 mg/kg body weight, 2 to 8 mg/kg, 3 to 7 mg/kg, or 4 to 6 mg/kg. The full-length anti-B7-H3 antibody is typically administered via infusion lasting for a period of 30 to 35 minutes. The frequency of administration may vary depending on the severity of the condition. The frequency may range from three times per week to once every 1 or 2 weeks.

In addition, the present invention relates to a method for preventing or treating cancer or tumor, autoimmune disease, or inflammatory disease, the method comprising: administering a therapeutically effective amount of the anti-B7-H3 antibody or antigen binding fragment thereof or the multi-specific antibody or the antibody-drug conjugate to a patient in need of the prevention or treatment of cancer or tumor, autoimmune disease, or inflammatory disease. The prevention or treatment method may further comprise identifying a patient in need of the prevention or treatment of the disease before the administration.

In some cases, by using the antibody or antigen binding fragment thereof in combination with other conventional anticancer therapeutic agents, a tumor cell expressing B7-H3 may be effectively targeted, and immune response may be enhanced by increasing anti-tumor T cell activity. The antibody or antigen binding fragment thereof may be used in combination with other anti-neoplastic agents or immunogenic agents, for example, attenuated cancer cells, tumor antigens (including recombinant proteins, peptides and carbohydrate molecules), antigen presenting cells (for example, dendritic cells pulsed with tumor-derived antigens or nucleic acids), immune stimulating cytokines (for example, IL-2, IFNα2, GM-CSF), and a cell transfected with a gene encoding immune stimulating cytokines; standard cancer therapy, for example, chemotherapy, radiation therapy or surgery; or other antibodies, for example, antibodies against PD-1, PD-L1, VEGF, EGFR, Her2/neu, VEGF receptors, other growth factor receptors, CD20, CD40, CTLA-4, OX-40, 4-IBB, and ICOS. The anti-B7-H3 antibody or antigen binding fragment thereof according to the present invention, and a pharmaceutical composition comprising the same may be administered simultaneously or sequentially with a conventional anticancer therapeutic agent.

In addition, the present invention provides a composition for diagnosing cancer or tumor, autoimmune disease, or inflammatory disease, comprising the anti-B7-H3 antibody or antigen binding fragment thereof, the antibody-drug conjugate or the multi-specific antibody, and a method for diagnosing the disease using the same.

Cancer or tumor, autoimmune disease, or inflammatory disease may be diagnosed by measuring the level of B7-H3 expression in a sample through the anti-B7-H3 antibody or antigen binding fragment thereof, the antibody-drug conjugate or the multi-specific antibody according to the present invention. The expression level may be measured according to a conventional immunoassay method, and it may be measured through radioimmunoassay using the antibody against B7-H3, radioimmunoprecipitation, immunoprecipitation, immunohistochemical staining, ELISA (enzyme-linked immunosorbent assay), capture-ELISA, inhibition or competition assay, sandwich assay, flow cytometry, immunofluorescence staining and immunoaffinity purification, but is not limited thereto. As a result of the immunoassay, when the expression of B7-H3 protein in a biological sample is higher than that in a normal biological sample (for example, normal tissue, blood, plasma, or serum), the diseases may be diagnosed.

In addition, the present invention provides a diagnostic kit comprising the diagnostic composition. The kit according to the present invention may include the anti-B7-H3 antibody or antigen binding fragment thereof according to the present invention, or an antibody-drug conjugate or a multi-specific antibody comprising the same, and a label for generating a detectable signal. The label may include a chemical bound to the antibody (for example, biotin), an enzyme (alkaline phosphatase, β-galactosidase, horseradish peroxidase, luciferase or cytochrome P450), a radioactive substance (for example, C14, I125, P32 and S35), a fluorescent substance (for example, fluorescein), a luminescent substance, a chemiluminescent substance, and FRET (fluorescence resonance energy transfer), but is not limited thereto. In this regard, for the substrate for the enzyme, when alkaline phosphatase is used as the enzyme, a chromogenic substrate such as bromochloroindolyl phosphate (BCIP), nitro blue tetrazolium (NBT), naphthol-AS-B1-phosphate and ECF (enhanced chemifluorescence) is used as the substrate, and when horseradish peroxidase is used, a substrate such as chloronaphthol, aminoethylcarbazole, diaminobenzidine, D-luciferin, lucigenin (bis-N-methylacridinium nitrate), resorufin benzyl ether, luminol, Amplex Red reagent (10-acetyl-3,7-dihydroxyphenoxazine), HYR (p-phenylenediamine-HCl and pyrocatechol), TMB (tetramethylbenzidine), ABTS (2,2'-Azine-di[3-ethylbenzthiazoline sulfonate]), o-phenylenediamine (OPD) and naphthol/pyronine, glucose oxidase and t-NBT (nitro bue tetrazolium) and m-PMS (phenzaine methosulfate) may be used, but is not limited thereto.

Cancer or tumor, autoimmune disease, or inflammatory disease may be diagnosed by analyzing the signal intensity displayed by the reaction between the sample and the antibody. Measurement of the activity or signal of an enzyme used for diagnosis may be performed according to various methods known in the art, through which B7-H3 expression may be analyzed qualitatively or quantitatively.

Hereinafter, the present invention will be described in more detail through the examples. These examples are only for illustrating the present invention, and the scope of the present invention is not limited by these examples.

Example 1: Expression and Purification of B7-H3 Antigen

Example 1-1: Construction of B7-H3 Protein Expression Vector

In order to clone only the extracellular domain of B7-H3, polymerase chain reaction (PCR) was performed using a Jurkat cell cDNA library (Stratagene, USA) and a primer pair for B7-H3 containing restriction enzyme SfiI sites at 5' and 3' (Table 1). Expression vectors each expressing a protein in which 8× His, human Fc, or mouse Fc was fused to the carboxy-terminus of the extracellular domain of B7-H3 were constructed using the obtained PCR product and the N293F vector (FIG. 1).

TABLE 1

| Primer for cloning B7-H3 | | |
|---|---|---|
| NAME | 5'→3') sequence | SEQ ID NO: |
| B7-H3-F | CTGGAGGTCCAGGTCCCTGAAGACC | 66 |
| B7-H3-F | GGCCTCTGGGGGGAATGTCATAGGC | 67 |

Example 1-2: Expression and Purification of B7-H3 Antigen

Transfection was performed using PEI (polyethylenimine, 23966, Polysciences) under optimized conditions. Human HEK293F cells were inoculated into a medium (#Freestyle 293 AGT type; AG100009P1, Thermo.) at $5\times10^5$ cells per ml and cultured until $1\times10^6$ cells/ml was reached. Each expression vector obtained in Example 1-1 was mixed with PEI to form a polyplex, and then transformed by adding to the cells, and then 5 g/L of Soytone (Soytone; #212488, DIFCO) was added, and then the cells were cultured for another 6 days. The expressed B7-H3-Fc antigens were sequentially purified using protein A agarose and Superdex 200 (1.5 cm*100 cm) gel filtration chromatography. Each antigen-producing culture solution was centrifuged at 8,000 rpm for 30 minutes to remove cell debris, and filtered using a bottle top filter having a 0.22 μm pore size. In order to perform purification, 3 ml of Ni-NTA resin (#30230, QIAGEN) was put into an empty column, and then the resin was packed with 20 ml of a binding buffer (10 mM imidazole). The culture solution filtered on the packed resin was flowed at a gravity-flow rate to bind to the resin at a rate of 0.2 ml per minute. Washing with 100 ml of a wash buffer (20 mM Imidazole) was performed, and then elution with an elution buffer (250 mM imidazole) was performed. The eluate obtained with the elution buffer was buffer exchanged with DPBS (Dulbecco's phosphate-buffered saline) through dialysis (1 L, 3 times). The concentration of the protein was measured by a Nano-drop. Each protein was purified using SDS-PAGE and size exclusion chromatography (#TSK-GEL G-3000 SWXL Size-exclusion chromatography (SEC), Tosoh), and the purity was identified, and all of them had a purity of at least 95%.

Example 2: Selection of B7-H3 Human Antibody

Example 2-1: Preparation of Antigen

50 μg of each of B7-H3-His prepared in Example 1 and B7-H3-his (#11188-H08H) and B7-H3-Fc (#11188-H02H) antigens purchased from Sino Biological Inc. was coated on an immunosorb tube, and then blocking was performed.

Example 2-2: Preparation of Human Antibody Library Phage

E. coli was infected with human scFv library phage (Y-Biologics) having a diversity of $2.7\times10^{10}$, and then the obtained E. coli was cultured at 30° C. for 16 hours. The culture solution was centrifuged, and the supernatant was concentrated with PEG (polyethylene glycol), and then dissolved in PBS (phosphate buffered saline) buffer solution to prepare a human antibody library phage.

Example 2-3: Biopanning

The library phage obtained in Example 2-2 was put into the immunosorb tube prepared in Example 2-1, and reacted at room temperature for 2 hours, and then washed with 1× PBST and 1× PBS, and then treated sequentially with 100 mM TAE and Tris-HCl (pH 7.5) solutions to elute only scFv-phages specifically bound to the antigen. A pool of positive phages was obtained through a panning process in which *E. coli* was again infected with the eluted phages and amplified, and the second and third rounds of panning were performed with the phages amplified in the first round of panning in the same manner, except that the number of times in the PBST (PBS+tween-20) washing step was increased. As a result, as shown in Table 2, it was found that the number of phages bound to the antigen was increased to a certain degree in the third round of panning.

TABLE 2

| Comparison of antibody titer according to panning | | |
| --- | --- | --- |
| Round of panning | Number of phages introduced | Number of phages bound |
| First round | $3 \times 10^{12}$ | $2 \times 10^5$ |
| Second round | $4 \times 10^{12}$ | $3 \times 10^6$ |
| Third round | $4 \times 10^{12}$ | $5 \times 10^7$ |

Example 2-4: Poly Phage ELISA

Poly phage ELISA was performed in order to examine the antigen specificity of the positive poly scFv-phage antibody pool obtained through each round of panning. ELISA was performed simultaneously with the phage pool obtained in each round using the immuno-plates coated with antigens B7-H3-His (Sino) and B7-H3-His (in house), respectively, and the immuno-plates coated with ITGA6-Fc protein used as an indicator of non-specific binding. As a negative control group of the ELISA, #38, an M13 phage with no antibody displayed, was also used.

Figure 2:
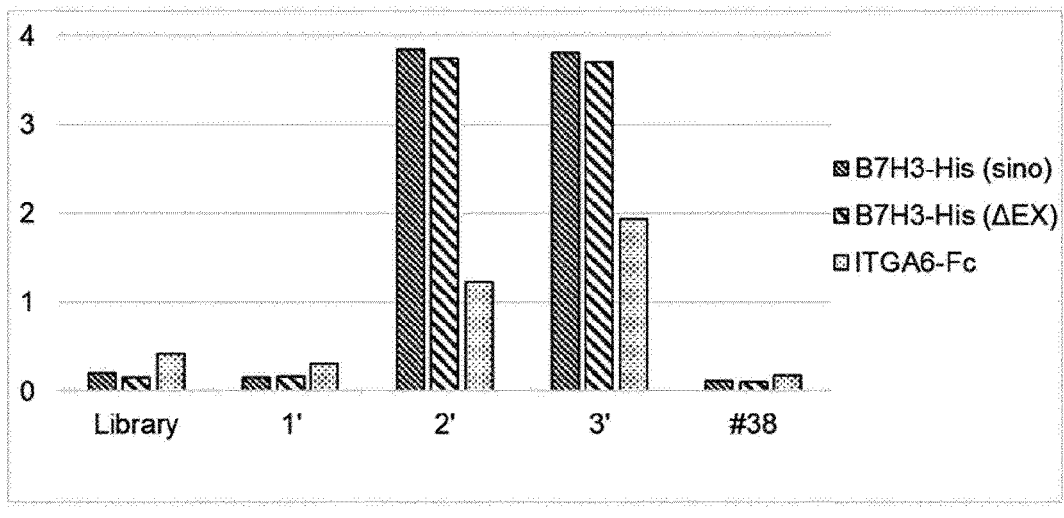
FIG. 2 illustrates a result obtained by measuring the binding ability of a poly scFV-phage to a B7-H3 antigen according to the number of panning.

As a result, as shown in FIG. 2, it was found that since the binding ability to the B7-H3-His antigen was increased from the positive phage pool of the second round panning, the anti-B7-H3 phage antibody was successfully increased.

Example 2-5: Selection of Positive Phage

Thousands of monoclones were selected from the positive phage pool of the third round panning, which was identified to have a high binding ability in the poly phage ELISA, and infected with a helper phage in a 96-deep well plate and cultured, and then the mono scFv-phage present in the supernatant was transferred to the immuno-plate coated with the B7-H3 antigen, and ELISA was performed. At this time, the mono phage ELISA for B7-H3-His (Sino) or B7-H3-His (in house) and the ELISA for the ITGA6-Fc protein, a non-specific antigen control group, were simultaneously performed, and it was identified whether the obtained positive phage clone was specific for B7-H3.

Figure 3:
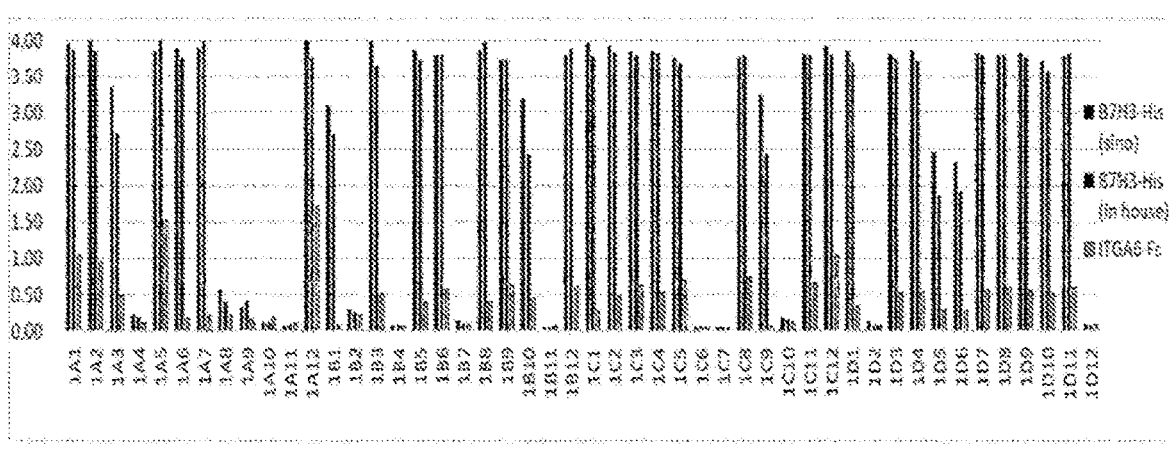
FIG. 3 illustrates a result obtained by measuring the B7-H3-His specific binding ability of a mono scFV-phage by ELISA.

As a result, as shown in FIG. 3, it was found that mono scFv-phage clones had a strong binding ability only to B7-H3-His, and dozens of preliminary antibody clones were selected. On the other hand, affinity-increasing panning of the CD276-039C05 clone selected for characterization was attempted to additionally secure excellent antibody clones.

Example 2-6: Nucleotide Sequence Analysis of Positive Phage Antibody

For the selected mono clone, the phagemid DNA was isolated using a DNA purification kit (Qiagen, Germany), and the nucleotide sequence was analyzed. As a result of analyzing the CDR3 region sequences of the heavy and light chains, clones as shown in Table 3 were identified.

TABLE 3

| Characteristics of B7-H3 mono clone | | | | |
| --- | --- | --- | --- | --- |
| ANTIBODY | GERMVH | HOMOVH | GERMVL | HOMOVL |
| CD276-0333E03 | IGHV3-23*04 | 95.9% (93/97) | IGLV2-14*01 | 93.8% (91/97) |
| CD276-040F10 | IGHV1-3*01 | 86.4% (82/96) | IGKV1-12*01 | 91.6% (87/95) |
| CD276-061H04 | IGHV3-49*04 | 86.0% (86/100) | IGKV1-5*03 | 94.7% (89/94) |
| CD276-039C05 | IGHV1-69*04 | 99.0% (96/97) | IGKV1-5*03 | 89.4% (84/94) |
| CD276-039C05_LS_001E10 | IGHV1-69*04 | 99.0% (96/97) | IGKV1-5*03 | 92.6% (88/95) |
| CD276-039C05_LS_002A11 | IGHV1-69*04 | 99.0% (96/97) | IGKV1-5*03 | 90.3% (84/93) |
| CD276-039C05_LS_002B07 | IGHV1-69*04 | 99.0% (96/97) | IGKV1-16*01 | 93.7% (89/95) |
| CD276-039C05_LS_002C07 | IGHV1-69*04 | 99.0% (96/97) | IGKV1-5*03 | 90.3% (84/93) |
| CD276-039C05_LS_002D03 | IGHV1-69*04 | 99.0% (96/97) | IGKV1-5*03 | 95.7% (90/94) |
| CD276-039C05_LS_002H07 | IGHV1-69*04 | 99.0% (96/97) | IGKV1-5*03 | 94.6% (88/93) |

On the other hand, the amino acid sequences of the CDRs and variable regions of the heavy and light chains are as described in Tables 4 and 5. The sequences of the poly-nucleotides encoding the heavy and light chain variable regions are shown in Table 6 below.

TABLE 4

| Amino acid sequence of heavy chain CDR and light chain CDR | | | |
| --- | --- | --- | --- |
| Antibody | | CDR sequence | SEQ ID NO: |
| CD276-033E03 | CDRH1 | GFTFSSYA | 13 |
| | CDRH2 | ISGSGGSR | 14 |
| | CDRH3 | ASHTIPGAWDV | 15 |

TABLE 4-continued

Amino acid sequence of heavy
chain CDR and light chain CDR

| Antibody | | CDR sequence | SEQ ID NO: |
|---|---|---|---|
| | CDRL1 | TRDVGGYNY | 16 |
| | CDRL2 | DVN | 17 |
| | CDRL3 | SSYTTSSRRV | 18 |
| CD276-040F10 | CDRH1 | GYTFSSYW | 1 |
| | CDRH2 | INPGNGHT | 2 |
| | CDRH3 | VADPRRPKVPTALFVY | 3 |
| | CDRL1 | QGIGTW | 4 |
| | CDRL2 | AAS | 5 |
| | CDRL3 | QQAINFPIT | 6 |
| CD276-051H04 | CDRH1 | GFNFHDYA | 7 |
| | CDRH2 | IRHQRYGGIT | 8 |
| | CDRH3 | ARGSSSSSWYLPNDY | 9 |
| | CDRL1 | QDISTW | 10 |
| | CDRL2 | KAS | 11 |
| | CDRL3 | QQYNRFWT | 12 |
| CD276-039C05 | CDRH1 | GGTFSSYA | 19 |
| | CDRH2 | IIPILGIA | 20 |
| | CDRH3 | ANGGDSSSWYTFDT | 21 |
| | CDRL1 | QSISRW | 22 |
| | CDRL2 | KAS | 11 |
| | CDRL3 | QQYNTFPLT | 23 |
| CD276-039C06_LS_001E10 | CDRH1 | GGTFSSYA | 19 |
| | CDRH2 | IIPILGIA | 20 |
| | CDRH3 | ANGGDSSWYTFDT | 21 |
| | CDRL1 | QTINSW | 24 |
| | CDRL2 | KAS | 11 |
| | CDRL3 | QQNSYSLT | 25 |
| CD276-039C05_LS_002A11 | CDRH1 | GGTFSSYA | 19 |
| | CDRH2 | IIPILGIA | 20 |
| | CDRH3 | ANGGDSSSWYTFDT | 21 |
| | CDRL1 | QNINSW | 26 |
| | CDRL2 | KAS | 11 |
| | CDRL3 | QQYDSNPLT | 27 |
| CD276-039C05_LS_002B07 | CDRH1 | GGTFSSYA | 19 |
| | CDRH2 | IIPILGIA | 20 |
| | CDRH3 | ANGGDSSSWYTFDT | 21 |

TABLE 4-continued

Amino acid sequence of heavy
chain CDR and light chain CDR

| Antibody | | CDR sequence | SEQ ID NO: |
|---|---|---|---|
| | CDRL1 | QGISSY | 28 |
| | CDRL2 | KAAS | 5 |
| | CDRL3 | QQYSFPLT | 29 |
| CD276-039C05_LS_002C07 | CDRH1 | GGTFSSYA | 19 |
| | CDRH2 | IIPILGIA | 20 |
| | CDRH3 | ANGGDSSSWYTFDT | 21 |
| | CDRL1 | QSIRW | 30 |
| | CDRL2 | KAY | 31 |
| | CDRL3 | QQYNTSPLT | 32 |
| CD276-039C05_LS_002D03 | CDRH1 | GGTFSSYA | 19 |
| | CDRH2 | IIPILGIA | 20 |
| | CDRH3 | ANGGDSSSWYTFDT | 21 |
| | CDRL1 | ETISSW | 33 |
| | CDRL2 | KAS | 11 |
| | CDRL3 | QQYYSYPIT | 34 |
| CD276-039C05_LS_002H07 | CDRH1 | GGTFSSYA | 19 |
| | CDRH2 | IIPILGIA | 20 |
| | CDRH3 | ANGGDSSSWYTFDT | 21 |
| | CDRL1 | QSIDNW | 35 |
| | CDRL2 | KAS | 11 |
| | CDRL3 | QQYDSNPLT | 36 |

TABLE 5

Amino acid sequence of heavy and
light chain variable regions

| Antibody | | Variable region sequence | SEQ ID NO: |
|---|---|---|---|
| CD276-033E03 | Heavy Chain | QVQLVESGGGLVQSG GSLRLSCAASGFTFS SYAMSWVRQAPGKGL EWVSVISGSGGSRYY ADSVKGRFTISRDNS KNTLYLQMNSLRAED RAVYYCASHTIPGAW DVWGQGTLVTVSS | 41 |
| | Light Chain | QSALTQPASVGSPGQ SITISCTGTTRDVGG YNYVSWYQQHPGKAP KLMIYDVNNRPSGVS YRFSGSKSGNTASLA SLTISGLQAEDEADY YCSSYTTSSRRVFGT GTKVTVL | 42 |

TABLE 5-continued

| Amino acid sequence of heavy and light chain variable regions | | | |
|---|---|---|---|
| Antibody | Variable region sequence | | SEQ ID NO: |
| CD276-040F10 | Heavy Chain | QVQLVESGAEVKKPG ASVKLSCKASGYTFS SYWMHWVRQAPGQRL EWMGEINPGNGHTNY NEKSKSRVTITVDKS ASTAVMELSSLRSED TAVYYCVADPRRPKV PTALFVYWGQGTLVT VSS | 37 |
| | Light Chain | DIQMTQSPSSVSASV GDRVTISCRASQGIG TWLAWYQQKPGKAPR LLIYAASSLDSGVPS RSSASGSGTDSTLTI SSLQPEDFATYYCQQ AINFPITFGQGTRLE IK | 38 |
| CD276-051H04 | Heavy Chain | QVQLVESGGGLVQPG RSLRLSCTTSGFNFH DYALSWVRQAPGKGL EWVSFIRHQRYGGTT QYAASVKGRFTISRD DSKGIAYLQMNSLRA EDTAVYYCARGSSSS SWYLPNDYWGQGTLV TSS | 39 |
| | Light Chain | DIQMTQSPSTLSASV GDRVTITCRASQDIS TWLAWYQQKPGKAPK LLIYKASSLQSGVPS RFSGSGSTEFTLTIS SLQPDDFATYYCQQY NRFWTFGQTKVEIK | 40 |
| CD276-039C05 | Heavy Chain | QVQLVESGAEVKKPG SSVKVSCKASGGTFS SYAISWVRQAPGQGL EWMGRIIPILGIANY AQKFQGRVTITADKS TSTAYMELSSLRSED TAVYYCANGGDSSSW YTFDYWGQGTLITVS S | 43 |
| | Light Chain | DIQMTQSPSTLSASV GDKLTLTCRASQSIS RWLAWYQQKPGKAPK LLIYKASYLQTGVPS RFSGSTGTEFTLTIS SLQPDDFATYYCQQY NTFPLTFAGGTKVEI K | 44 |
| CD276-039C06_ LS_001E10 | Heavy Chain | QVQLVESGAEVKKPG SSVKVSSKASGGTFS SYAISWVRQAPGQGL EWMGRIIPILGIANY AQKFQGRVTITADKS TSTAYMELSSLRSED TAVYYCANGGDSSSW YTFDYWGQGTLITVS S | 43 |
| | Light Chain | DIQMTQSPSTLSASV GDRVNITCRASQTIN SWLAWYQQKPGKAPK LLIYKASYLQTGVPS RFSGSGAGTEFTLTI SSLQPDDFATYYCQQ | 45 |

TABLE 5-continued

| Amino acid sequence of heavy and light chain variable regions | | | |
|---|---|---|---|
| Antibody | Variable region sequence | | SEQ ID NO: |
| | | NYSYSLTFGGGTKVE IK | |
| CD276-039C05_ LS_002A11 | Heavy Chain | QVQLVESGAEVKKPG SSVKVSCKASGGTFS SYAISWVRQAPGQGL EWMGRIIPILGIANY AQKFQGRVTITADKS TSTAYMELSSLRSED TAVYYCANGGDSSSW YTFDYWGQGTLITVS S | 43 |
| | Light Chain | DIQMTQSPSTLSASV GDRLTITCRASQNIN SWLAWYQQKPGKAPK LLIYKASYLQTGVPS RFSGSGSTEFTLTI TSSLQPDDFASYYCQ QYDSNPLTFGGGTKV EIK | 46 |
| CD276-039C05_ LS_002B07 | Heavy Chain | QVQLVESGAEVKKPG SSVKVSCKASGGTFS SYAISWVRQAPGQGL EWMGRIIPILGIANY AQKFQGRVTITADKS TSTAYMELSSLRSED TAVYYCANGGDSSSW YTFDYWGQGTLITVS S | 43 |
| | Light Chain | DIQMTQSPSSLSASV GDRVTITCRASQGIS SYLAWYQQKPGKAPK LLIYAASTLQSGVPS RFSGSGSGTDFTLTI SSLQPEDFATYYCQQ YYSFPLTFGGGTKVE IK | 47 |
| CD276-039C05_ LS_002C07 | Heavy Chain | QVQLVESGAEVKKPG SSVKVSCKASGGTFS SYAISWVRQAPGQGL EWMGRIIPILGIANY AQKFQGRVTITADKS TSTAYMELSSLRSED TAVYYCANGGDSSSW YTFDYWGQGTLITVS S | 43 |
| | Light Chain | DIQMTQSPSTLSASV VGDRVTITCRAGQSI RSWLAWYQQKPGEAP KLLIYKAYYLQTGVP SRFSGSGAGTEFTLL TISSLQPDDFATYYC QQNTSPLTFGGGTKV EIK | 48 |
| CD276-039C05_ LS_002D03 | Heavy Chain | QVQLVESGAEVKKPG SSVKVSCKASGGTFS SYAISWVRQAPGQGL EWMGRIIPILGIANY AQKFQGRVTITADKS TSTAYMELSSLRSED TAVYYCANGGDSSSW YTFDYWGQGTLITVS S | 43 |
| | Light Chain | DIQMTQSPSTLSASV GDRVTITCRASETIS SWLAWYQQKPGKAPK | 49 |

TABLE 5-continued

Amino acid sequence of heavy and
light chain variable regions

| Antibody | | Variable region sequence | SEQ ID NO: |
|---|---|---|---|
| | | LLIYKASSLQSGVPS RFSGSGSGTEFTLTI SSLQPDDFATYYCQQ YYSYPITFGQGTRLE IK | |
| CD276-039C05_ LS_002H07 | Heavy Chain | QVQLVESGAEVKKPG SSVKVSCKASGGTFS SYAISWVRQAPGQGL EWMGRIIPILGIANY AQKFQGRVTITADKS TSTAYMELSSLRSED TAVYYCANGGDSSSW YTFDYWGQGTLITVS S | 43 |
| | Light Chain | DIQMTQSPSLTSASV GDRVTITCRASQSID NWLAWYQQKPGKAPK LLIYKASSLQSGVPS RFSGSGSGTEFTLTI SSLQPDDFASYYCQQ YDSNPLTFGGGTKVE IK | 50 |

TABLE 6

Sequence of polynucleotide encoding heavy
and light chain variable regions

| Antibody | | SEQ ID NO: |
|---|---|---|
| CD276-033E03 | Heavy Chain | 51 |
| | Light Chain | 52 |
| CD276-040F10 | Heavy Chain | 53 |
| | Light Chain | 54 |
| CD276-051H04 | Heavy Chain | 55 |
| | Light Chain | 56 |
| CD276-039C05 | Heavy Chain | 57 |
| | Light Chain | 58 |
| CD276-039C05_LS_001E10 | Heavy Chain | 57 |
| | Light Chain | 59 |
| CD276-039C05_LS_002A11 | Heavy Chain | 57 |
| | Light Chain | 60 |
| CD276-039C05_LS_002B07 | Heavy Chain | 57 |
| | Light Chain | 61 |
| CD276-039C05_LS_002C07 | Heavy Chain | 57 |
| | Light Chain | 62 |
| CD276-039C05_LS_002D03 | Heavy Chain | 57 |
| | Light Chain | 63 |
| CD276-039C05_LS_002H07 | Heavy Chain | 57 |
| | Light Chain | 64 |

Example 3: Production of B7-H3 Human Antibody

Example 3-1: Conversion of scFv form to IgG form

In order to convert the monoclonal phage antibody selected in Example 2 from a scFv form to an IgG form, N293F HC vector was prepared by cloning the nucleotide sequence of the heavy chain variable region into pNATVH (Y-Biologics) using restriction enzyme SfiI/NheI site, and N293F LC vector was prepared by cloning the nucleotide sequence of the light chain variable region into pNATVL (Y-Biologics) using restriction enzyme SfiI/BglII site.

Example 3-2: Production and Purification of Human Antibody

Figure 4:
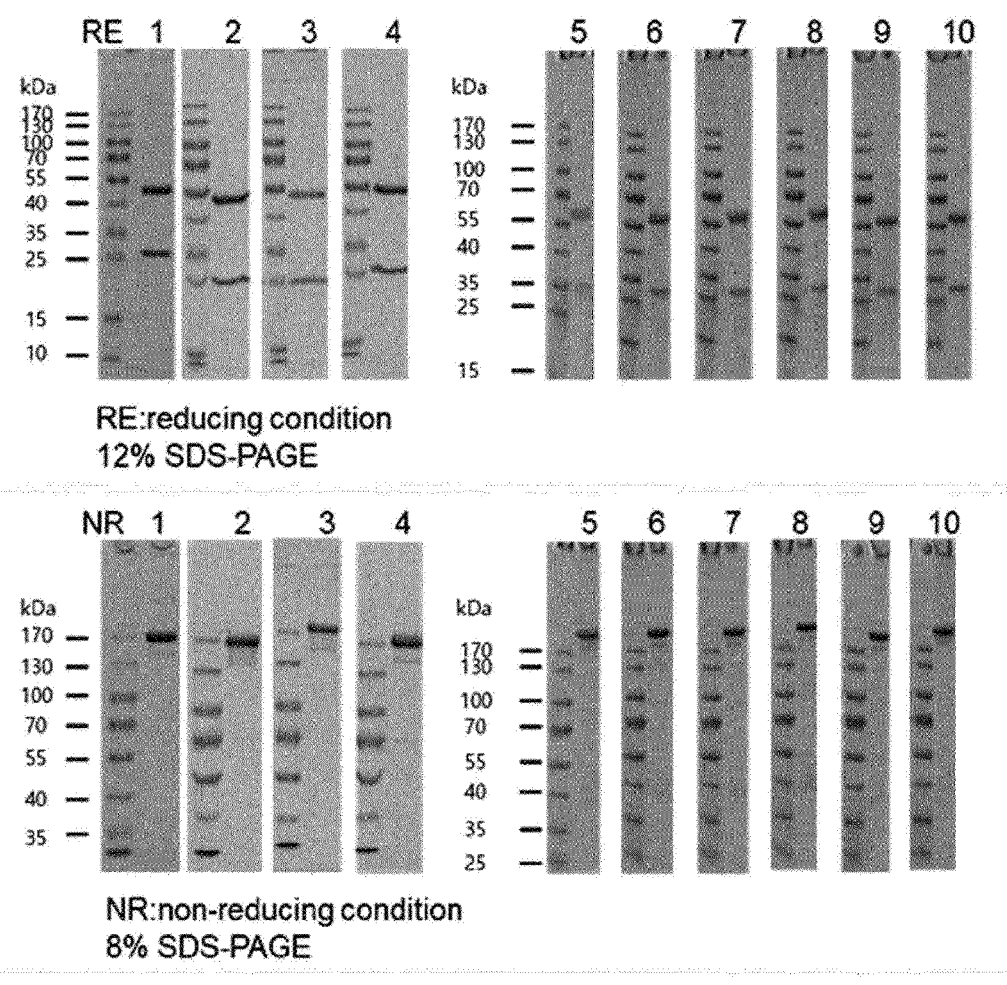
FIG. 4 illustrates a result obtained by identifying the selected B7-H3 antibodies by SDS-PAGE.

HEK293F cells were co-transfected with the N293F HC and N293F LC vectors, and the culture solution was collected on the 7th day of culture, and the cells and the suspended matter were removed through centrifugation and 0.22 μm Top-filter filtration, and then the supernatant was combined and purified by protein A bead. The purity of the anti-B7-H3 antibody was analyzed using SDS-PAGE (FIG. 4).

(1) Protein A Chromatography

The culture solution was centrifuged at 8,000 rpm for 30 minutes to remove cell debris, and filtered using a bottle top filter (Steritop-GP Filter Unit. #SCGPS01RE, Millipore) having a 0.22 μm pore size. On the other hand, 4 ml of protein A Sepharose resin slurry (KANEKA KanCapA™, Cat. No. KKC20170403_01) was put into an empty column (#BR731-1550, Bio-rad), and then the resin was packed and washed with 100 ml of DPBS (#LB001-02). The filtered medium was loaded on the packed resin and flowed at a rate of 1 ml per minute (#EP-1 Econo pump, Bio-Rad). After washing with 150 ml of DPBS, it was eluted with 10 ml of 0.1 M glycine-HCl (pH 3.3). 10% of 1 M Tris-HCl (pH 9.0) was added to the eluate to neutralize the pH, and the buffer was exchanged with DPBS using Amicon Ultra-10 (#UFC901096, Millipore). After carrying out this process about 3 times, it was stopped when it was concentrated to about 1 ml, and the concentration was measured by a Nano-drop.

(2) SDS-PAGE

SDS-PAGE was performed in order to identify the purity of the purified protein. 3 μg of the purified protein sample was mixed with 5 μL of the reducing sample buffer and the non-reducing sample buffer, respectively, and boiled at 100° C. for 3 minutes. 12% gel was loaded into the running tank (#165-8027, Bio-Rad), and 1× running buffer was filled into the inside of the gel and filled to about ⅓ of the outside of the gel, and the prepared sample was loaded into the wells using a pipette, while preventing bubbles from entering. 4 μL of AccuBand Prestained Protein Marker was loaded into the leftmost well. The top cover of the gel chamber was mounted, and the power was connected to run at 200V, 1 hr conditions. After one hour, the gel was separated from the tank, immersed in the staining buffer, and stained for 1 hour on a stirrer. Thereafter, the staining solution was discarded, and the color was decolorized while stirring with the decolorizing solution for about 1 hour, and the decolorizing solution was exchanged once more to decolorize again. The decolorized gel was washed with distilled water, and then the image was saved using an imaging device.

(3) Western Blotting

The SDS-PAGE was run for 1 hour as in (2), and then the gel was separated from the tank, the NC membrane was placed under the gel, the cassette was fixed and put into the transfer tank (#165-8027, Bio-Rad), and the transfer buffer was filled into the inside thereof and then run for about 2 hours at 110V. When it was expected that the transfer was completed, the transfer was stopped, and the NC membrane was taken out and blocked with a blocking solution (1% Skim milk/PBS) at room temperature for 1 hour. Thereafter, the secondary antibodies, anti-hFc-HRP (#31413, Thermo) and anti-His-HRP (#A7058, Sigma), were diluted to 1:4000 with the blocking solution, and then put on the NC membrane, and reacted at room temperature for 1 hour. The NC membrane was washed 5 times with 1× PBST at 10 ml each. Thereafter, the ECL solution (#16024, Intron) was scattered on the NC membrane, and then detected using a Chemi Doc (UVITEC, mini HD) with exposure times of 1 sec, 30 sec, and 1 min, and the best images were selected and saved.

Example 4: Characteristics of B7-H3 Monoclonal Antibody

Example 4-1: Specific Binding Force to Human B7-H3 Expressed on Cell surface (FACs)

Figure 5:
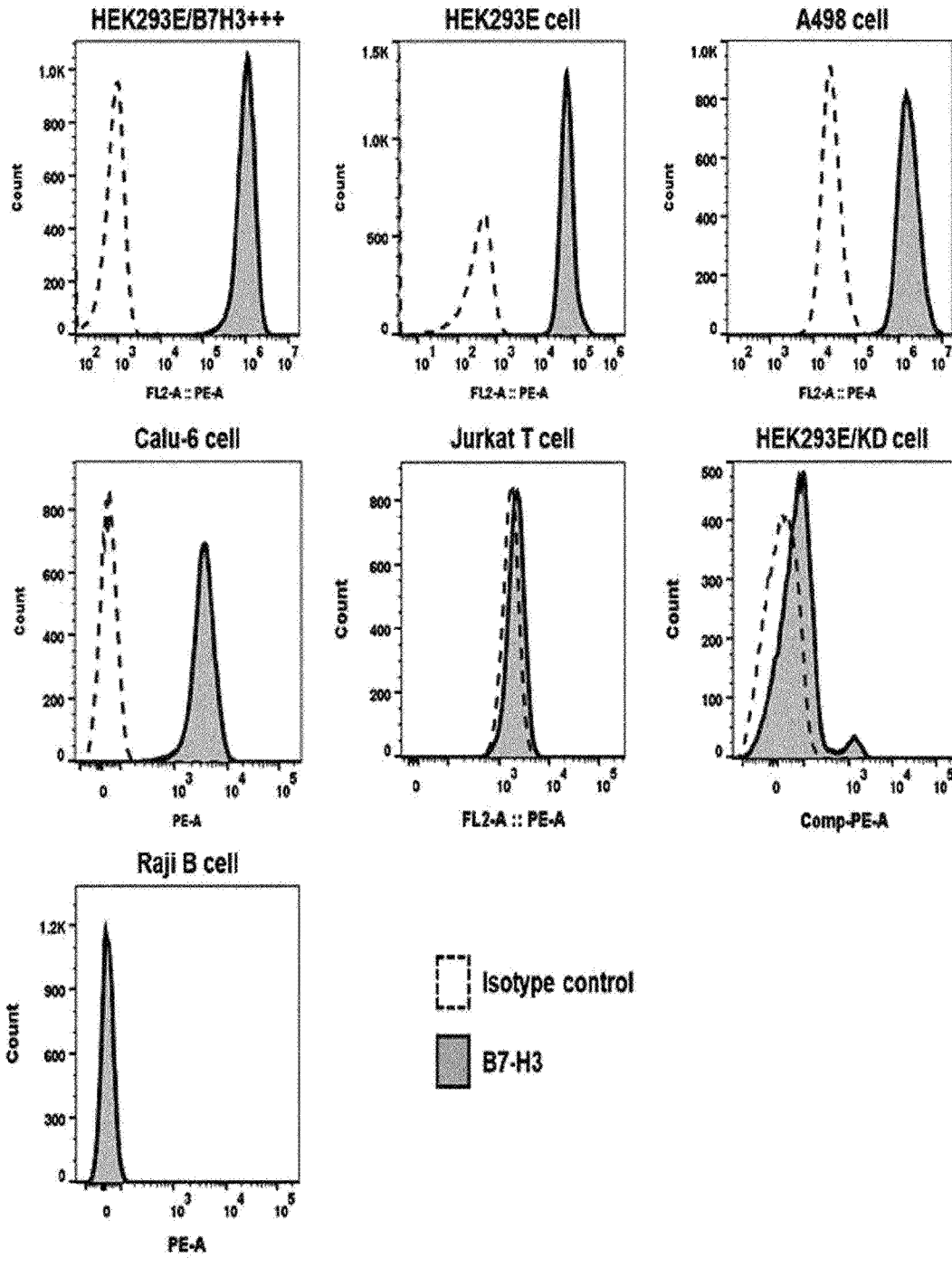
FIG. 5 illustrates a result obtained by measuring the expression rate of B7-H3 for each cell line by FACs.
Figure 6A:
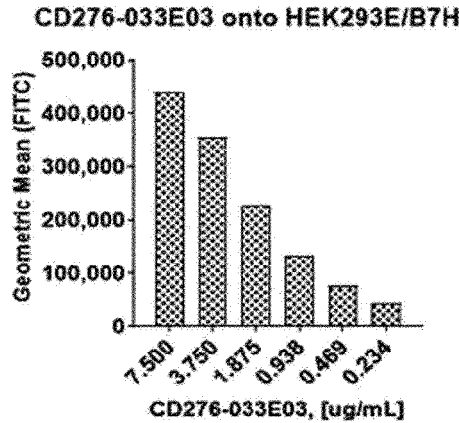
FIGS. 6a to 6d illustrate results obtained by measuring the binding force of the selected B7-H3 antibodies to the cell surface B7-H3 by FACs.
Figure 6A:
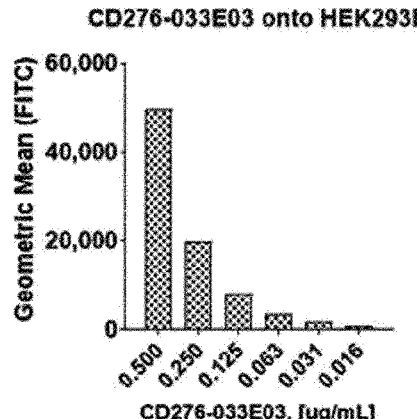
Figure 6B:
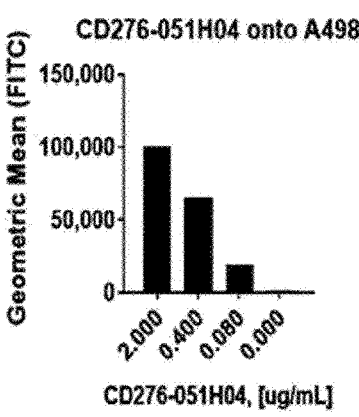
Figure 6B:
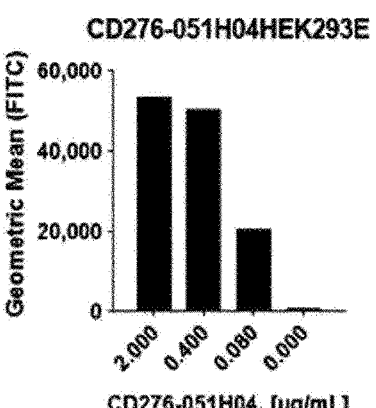
Figure 6B:
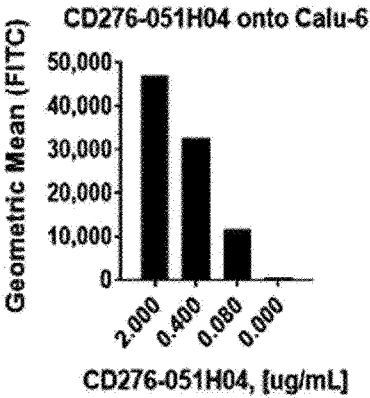
Figure 6B:
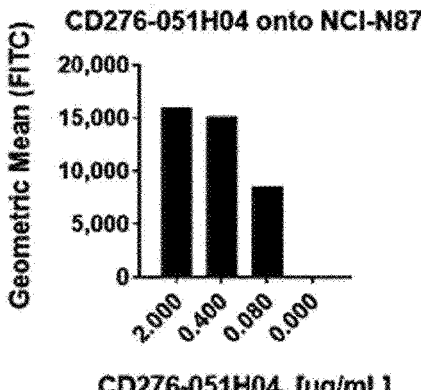
Figure 6C:
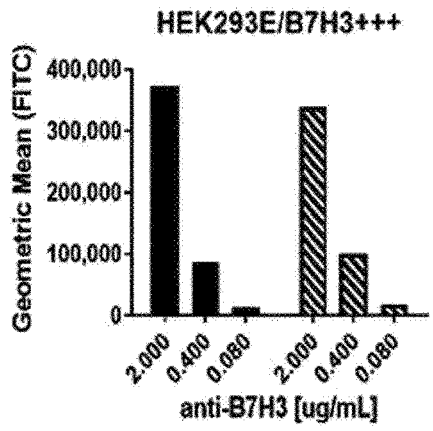
Figure 6C:
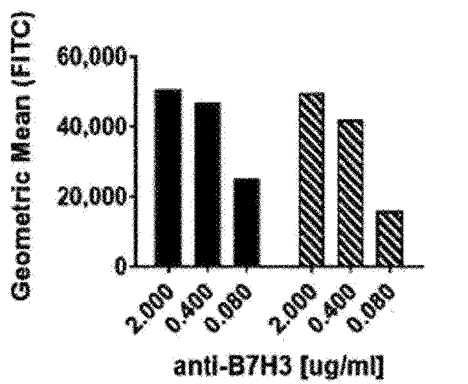
Figure 6C:
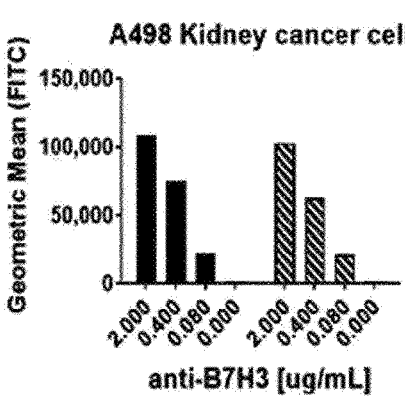
Figure 6C:
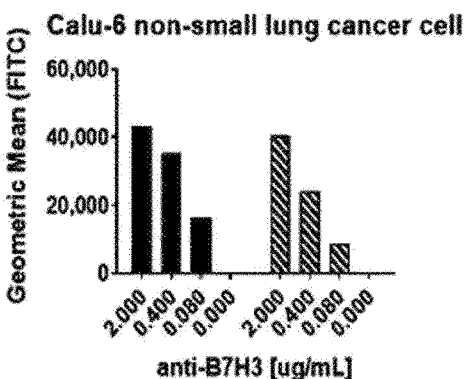
Figure 6C:
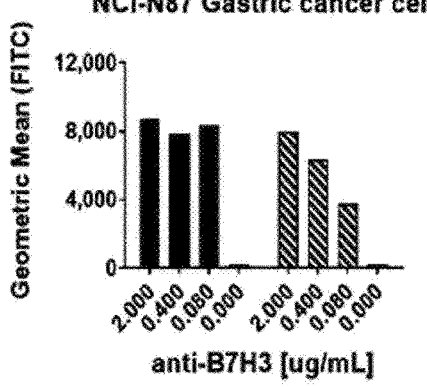
Figure 6D:
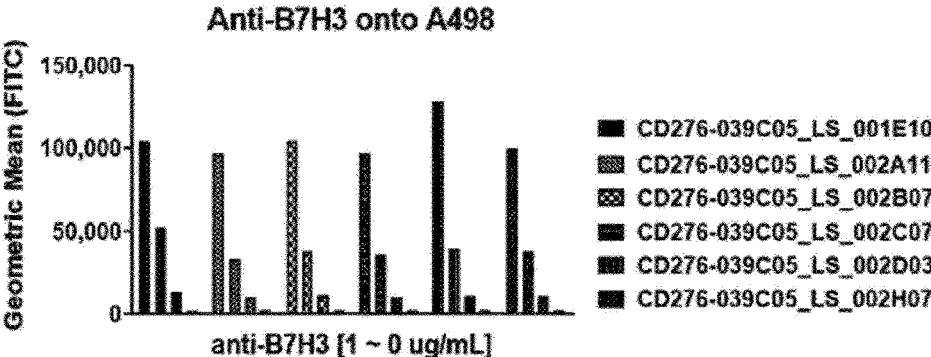
Figure 6D:
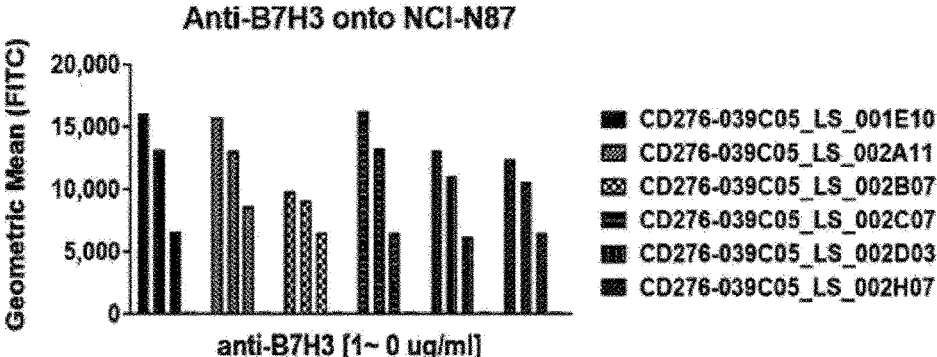
Figure 7A:
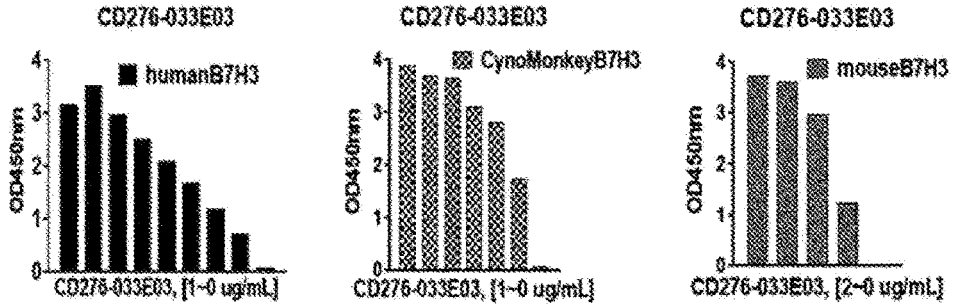
FIGS. 7a to 7e illustrate results obtained by measuring the binding force of the selected B7-H3 antibodies with several types of B7-H3 antigens by ELISA.
Figure 7B:
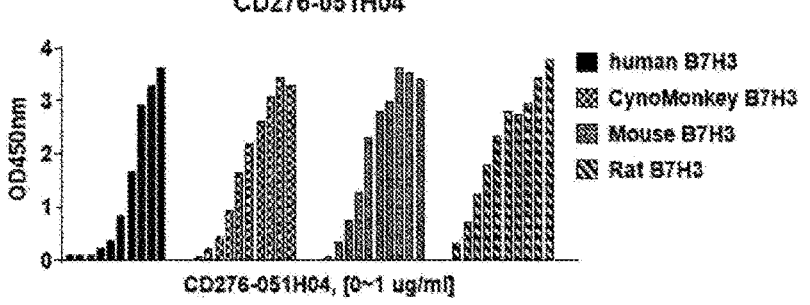
Figure 7C:
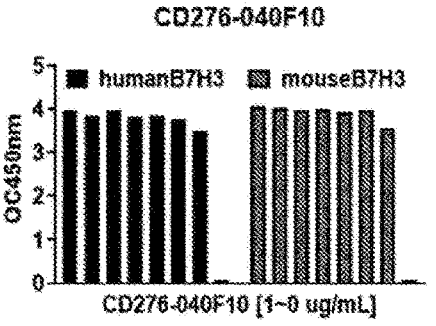
Figure 7D:
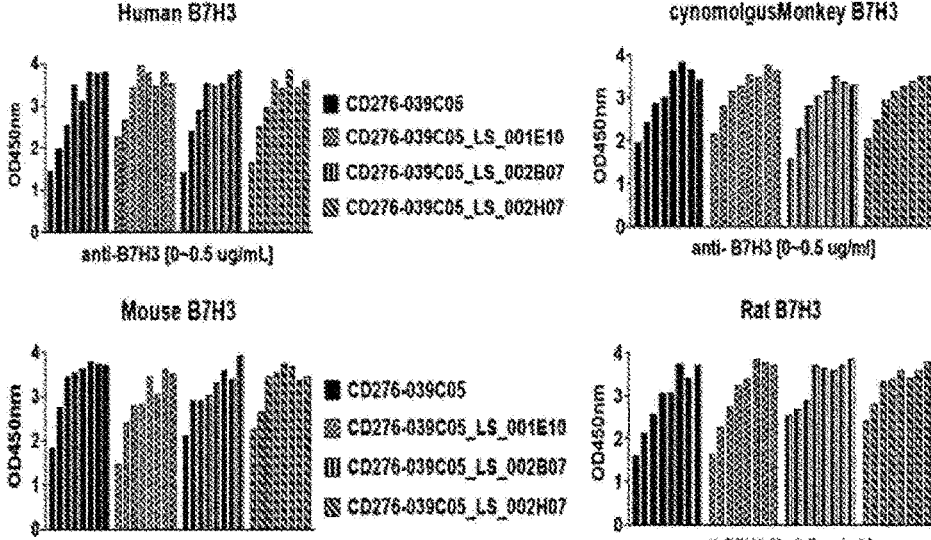
Figure 7E:
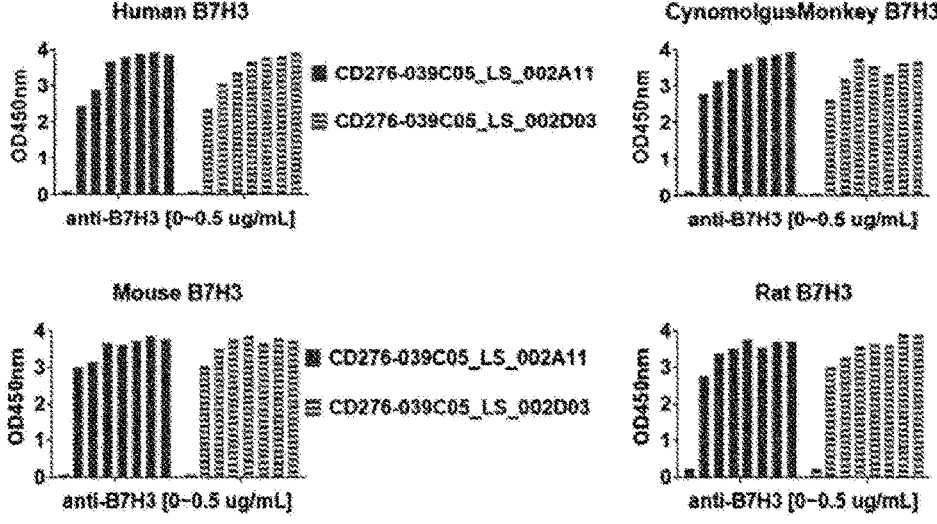

Each of the cells expressing human B7-H3 was prepared so as to be $0.5\times10^6$ cells per sample, and each of the antibodies was diluted to a certain factor and then reacted with the prepared cells at 4° C. for 30 minutes. Thereafter, the cells were washed three times with PBS (#LB001-02, welgene) containing 2% fetal bovine serum, and reacted at 4° C. for 20 minutes using an anti-human IgG antibody (#FI-3000, Vectorlabs) or a PE-anti-hIgG antibody (#555787, BD) to which FITC (fluorescein isothiocyanate) fluorescent substance was bound, and then washed in the same manner as above. The cells were suspended in PBS containing 0.5 ml of 2% FBS (#26140-079, Thermo), and then the binding force was analyzed using a flow cytometer, FACSCanto II flow cytometer (BD Biosciences, USA). As a result, it was found through geometric mean values that the B7-H3 antibody was bound to B7-H3 expressed on the cell surface in a concentration-dependent manner, and the B7-H3 antibody was not bound to Raji cells in which B7-H3 was not expressed, Jurkat cells in which B7-H3 was almost not expressed, and HEK293E/KD cell line in which B7-H3 was knocked down through shRNA (GIPZ human CD276 shRNA transfection starter kit, #V3LHS_306029, Thermo) (FIGS. 6a to 6d, and Table 7 below). The expression of B7-H3 in each cell line was measured using an anti-human CD276 antibody (#331606, Biolegend) to which a PE fluorescent substance was bound (FIG. 5).

TABLE 7

FACS binding force of B7-H3 antibody in cell line with no or low B7-H3 expression

| Cell line | ANTIBODY [2 ug/mL] | Geometric mean |
|---|---|---|
| Raji B cell | Human IgG | 8.48 |
| | CD276-033B03 | 8.58 |
| Jurkat T cell | Human IgG | 60.7 |
| | CD276-033B03 | 62.8 |
| HEK293E/KD cell | Human IgG | 20.5 |
| | CD276-033B03 | 29.6 |
| Raji B cell | Human IgG | 571.3 |
| | CD276-033C05 | 1190.6 |
| | CD276-040F10 | 548.3 |
| | CD276-051H04 | 497.9 |
| Jurkat T cell | Human IgG | 84.4 |
| | CD276-039C05 | 98.6 |
| | CD276-040F10 | 87.3 |
| | CD276-051H04 | 85.5 |
| Jurkat T cell | Human IgG | 35.1 |
| | CD276-039C05_LS_001E10 | 37.1 |
| | CD276-039C05_LS_002A11 | 39.2 |
| | CD276-039C05_LS_002B07 | 40.0 |
| | CD276-039C05_LS_002C07 | 39.9 |
| | CD276-039C05_LS_002D03 | 69.6 |
| | CD276-039C05_LS_002H07 | 40.8 |

Example 4-2: Thermostability of Anti-B7-H3 Antibody

The thermostability of the antibody was tested using differential scanning fluorimetry. The antibody protein was diluted in DPBS to make 3 μM, 45 μL and mixed with 5 μL of 200× sypro orange dye (#S6650, Thermo), and 50 μL was aliquoted into each qPCR tube (#TLS0851-white, Bio-Rad), and the lid (#TCS0803, Bio-Rad) was closed. qPCR was performed using a Biorad CFX96 real-time PCR instrument. qPCR was completed by reacting at 25° C. for 30 seconds, and then reacting for 0.5 minutes at each temperature with an increment by 0.5° C. to 99° C., and finally reacting at 25° C. for 10 seconds. The melting temperature (Melt Tm) was used as the rate constant for the unwinding of the antibody structure. The results are shown in Table 8 below.

TABLE 8

Melting temperature (Melt Tm)

| SAMPLE | Melt Tm (° C.) |
|---|---|
| DPBS | |
| CD276-033E03 | 65 |
| CD276-040F10 | 67 |
| CD276-051H04 | 68 |
| CD276-039C05 | 66 |
| CD276-039C05_LS_001E10 | 67 |
| CD276-039C05_LS_002B07 | 67 |
| CD276-039C05_LS_002H07 | 66 |

Example 4-3: Affinity for B7-H3 Antigen (OCTET)

The binding affinity of the antibody to B7-H3 antigen was measured based on the principle of BLI (biolayer interferometry) using an Octet QK instrument (Fortebio Inc.). The selected anti-B7-H3 antibody was immobilized on an AHC (Anti-Human IgG Fc Capture) biosensor (Fortebio Inc.), and human B7-H3 antigen prepared for each concentration was bound thereto, and the affinity (KD) was obtained. For all buffers, Kinetic Buffer (Fortebio Inc.) was used. First, the biosensor was immersed in a buffer to stabilize it, and the anti-B7-H3 antibody dissolved in the buffer at a concentration of 10 μg/ml was reacted for about 5 minutes and immobilized on the AHC biosensor. The biosensor was washed with a buffer for 3-5 minutes to remove the unimmobilized antibody, and the binding reaction was performed with the B7-H3 antigen prepared for each concentration (30 nM~0.24 nM) for 10 minutes, and then the dissociation reaction was performed for 10 minutes. All experiments were performed at 30° C., 1,000 rpm conditions, and sensorgram data was collected during the association and dissociation process over time. The equilibrium dissociation constant (KD) was obtained by applying a 1:1 global binding fitting model according to Octet data analysis software 9.0. As a result, the KD value was 0.04~2.0 nM, showing a high affinity for the B7-H3 antigen. The results are shown in Table 9 below.

TABLE 9

Affinity of anti-B7-H3 antibody for B7-H3 antigen (OCTET)

| NAME | $K_D$ (M) | Kon (1/Ms) | Koff (1/s) |
|---|---|---|---|
| CD276-033E03 | $2 \times 10^{-9}$ | $1 \times 10^6$ | $2 \times 10^{-4}$ |
| CD276-040F10 | $6 \times 10^{-11}$ | $7 \times 10^6$ | $4 \times 10^{-5}$ |
| CD276-051H04 | $3 \times 10^{-10}$ | $1 \times 10^6$ | $4 \times 10^{-4}$ |
| CD276-039C05 | $4 \times 10^{-11}$ | $6 \times 10^5$ | $3 \times 10^{-5}$ |
| CD276-39C05_LS_001E10 | $6 \times 10^{-11}$ | $1 \times 10^6$ | $7 \times 10^{-5}$ |
| CD276-39C05_LS_002A11 | $1.2 \times 10^{-10}$ | $1.3 \times 10^6$ | $1.5 \times 10^{-4}$ |
| CD276-39C05_LS_002B07 | $2 \times 10^{-10}$ | $3 \times 10^6$ | $6 \times 10^{-4}$ |
| CD276-39C05_LS_002D03 | $3.0 \times 10^{-10}$ | $1.6 \times 10^6$ | $4.7 \times 10^{-4}$ |
| CD276-39C05_LS_002H07 | $3 \times 10^{-10}$ | $9 \times 10^5$ | $3 \times 10^{-4}$ |

Example 4-4: Binding force for B7-H3 Antigen (ELISA)

His tagged B7-H3 was put into the wells of Pierce™ Nickel Coated Plates (#15142, pierce) and coated at room temperature for 1 hour, or Fc tagged B7-H3 was put into the wells of Immune plate (#439454, Thermo) and coated at 4° C. overnight. Mouse B7-H3 (#50973-M08H, Sino), rat B7-H3 (#80380-R08H, Sino), cynomolgus B7-H3 (#90806-C08H, Sino), and Human B7-H3 (#S1435, Y-Biologics) were used as antigens. After washing three times with a washing solution (PBS containing 0.05% tween-20 (#P9416, Sigma-Aldrich)), depending on the conditions, 300 µL of the blocking solution, 4% skim milk (#232120, Becton, Dickinson and Company)/PBS, was added, and allowed to stand at room temperature for 1 hour to block non-specific binding. The serially diluted antibody at a certain dilution factor was added and reacted by rocking at room temperature for 1 hour. It was washed in the same manner, and the HRP-conjugated anti-human Kappa antibody (#A7164, Sigma) was added and allowed to stand at room temperature for 1 hour. After washing 5 times with the washing solution, the TMB substrate solution (#T0440-1L, Sigma) was added and reacted at room temperature for at least 3 minutes under the light shield condition, and the color development was identified, and the reaction was stopped by adding 1 normal sulfuric acid solution (#S1478, Samchun). Absorbance was measured at 450 nm using a spectrophotometer (#GM3000, Promega or SpectraMaxM5, Molecular devices). It was found that the selected monoclonal B7-H3 antibody had a concentration-related binding force not only to the human B7-H3 antigen but also to the mouse, rat, and cynomolgus monkey B7-H3 antigens (FIGS. 7a to 7e).

Example 4-5: Binding Force for FcRN by pH (ELISA)

Figure 8:
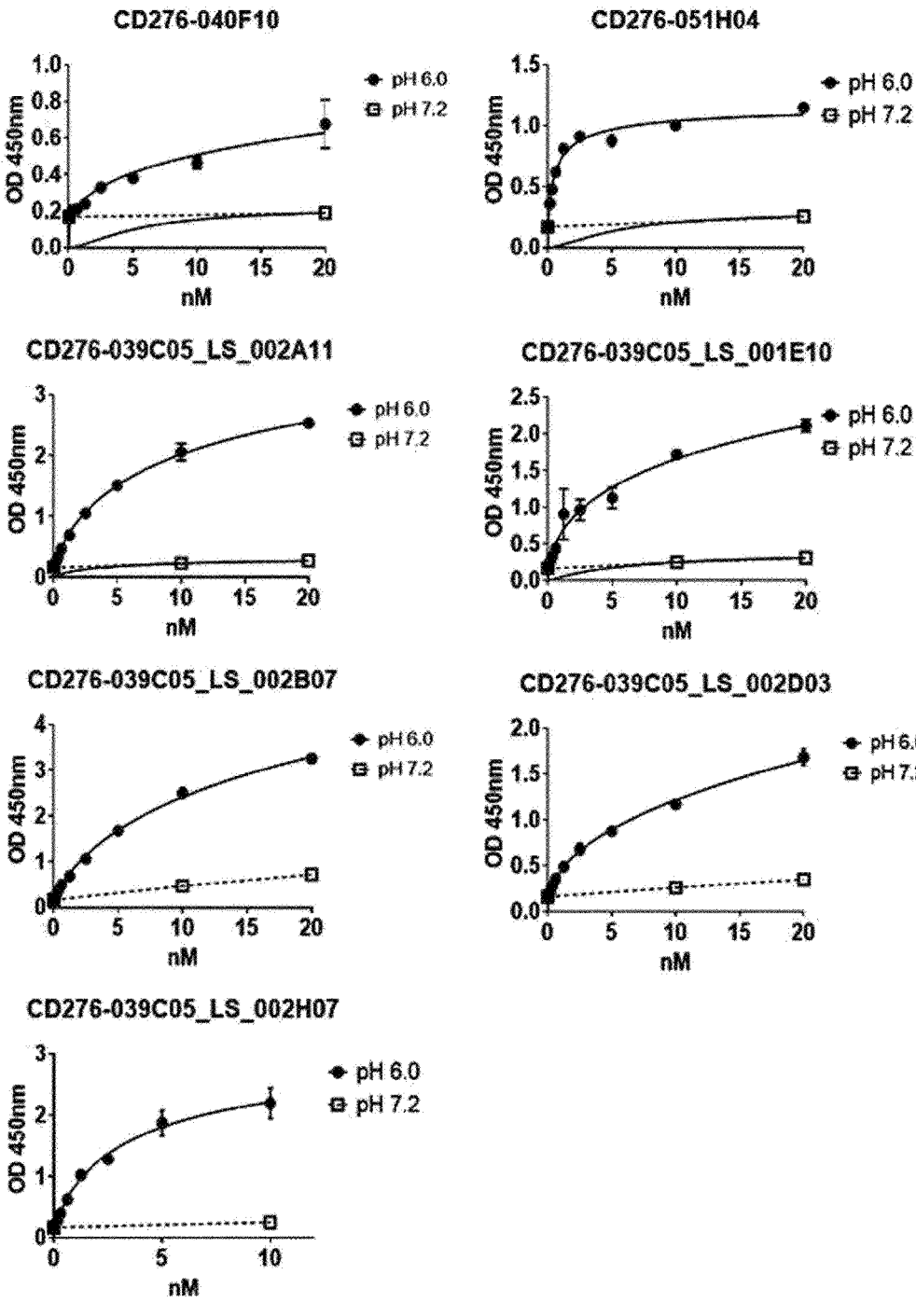
FIG. 8 illustrates a result obtained by measuring the binding force of the selected B7-H3 antibodies with the FcRn complex protein by ELISA.

Biotin was conjugated to FCGRT & B2M Heterodimer protein (#CT009-H08H, Sino) using EZ-Link Sulfo-NHS-Biotin (#15508, Thermo), and then 0.5 mg/mL was prepared, and 100 uL was put into each well of a Pierce™ NeutrAvidin™ Coated High Capacity Plate blocked with Ovalbumin (#A5503, Sigma) and coated with rocking at room temperature 2 hours. Each well was washed three times with sodium phosphate solution titrated to pH 6.0 and pH 7.2, and then 100 ul of the antibody diluted in each solution to a certain factor was put into each well and reacted with rocking at room temperature for 1 hour. After washing three times with each solution, 100 uL of 1:5000 diluted Peroxidase AffiniPure F(ab')₂ Fragment Goat Anti-Human IgG (H+L) (#109-036-003, Jackson) was put into each well and reacted with rocking at room temperature 1 hour. It was washed three times with pH 6.0 sodium phosphate solution, and TMB substrate was added and reacted under the light shield condition. When a color change was observed, the reaction was stopped with 0.5 M/L sulfuric acid solution. Absorbance was measured at 450 nm using the Glomax™ Discover system (#GM3000, Promega). It was found that the anti-B7-H3 antibody bound to the FcRN-B2M complex in a concentration-dependent manner only at pH 6.0 and did not bind at pH 7.2 (FIG. 8).

Example 4-6: Endocytosis of B7-H3 Antigen-Antibody Complex (Incucyte)

Figure 9A:
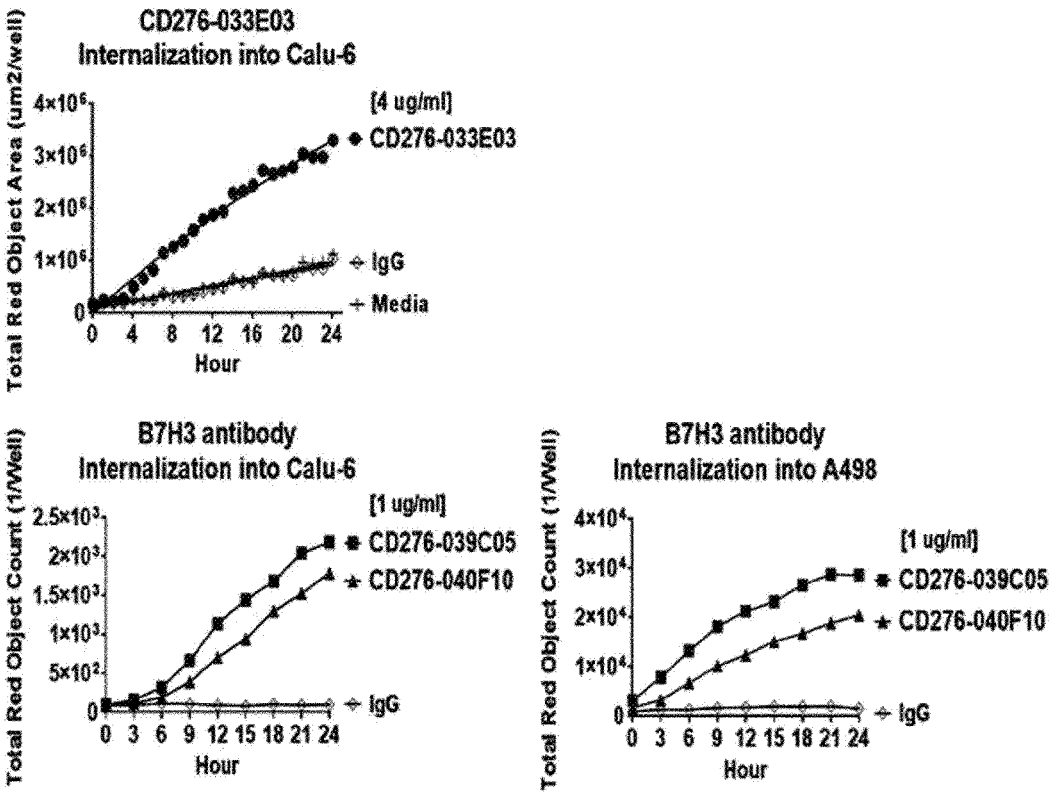
FIGS. 9a and 9b illustrate results obtained by measuring the endocytosis of the complex of the selected B7-H3 antibodies and the cell surface B7-H3 antigen.
Figure 9B:
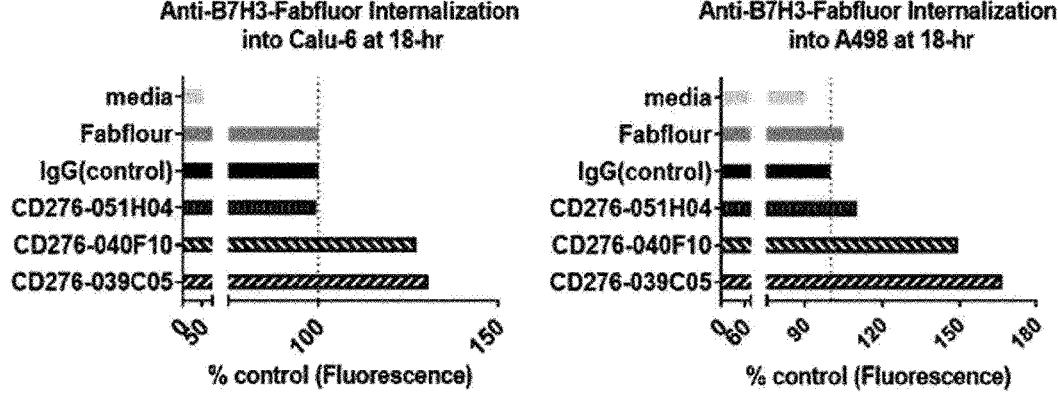

Calu-6 cell line was diluted in 1 ml of a growth medium (RPMI1640 (#A10491-01, Gibco), 10% FBS (#26140-079, Gibco), 1× Antibiotic-Antimycotic (#15240-062, Gibco), 100× MEM NEAA (#11140-050, Gibco)) to be 1, 2, or $4×10^5$ cells, and then 50 µL was put into each well of a 96-well plate (#3595, Corning) and cultured in a $CO_2$ incubator at 37° C. for at least 24 hours. A498 cell line was diluted in 1 ml of a growth medium (DMEM (#SH30243.01, Hyclon™), 10% FBS (#26140-079, Gibco), 1× Antibiotic-Antimycotic (#15240-062, Gibco), 100× MEM NEAA (#11140-050, Gibco)) to be 1, 2, or $4×10^4$ cells, and then 50 µL was put into each well of a 96-well plate (#3595, Corning) and cultured in a $CO_2$ incubator at 37° C. for at least 24 hours. On the other hand, the antibody to be tested and IncuCyte™ FabFluor Red (#4722, essen bioscience) were mixed in a molar ratio of 1:3 and allowed to stand at 37° C. for 15 minutes, and then 50 µL was carefully added to the well containing the cells. The plate was put into a $CO_2$ incubator equipped with IncuCyte ZOOM (essen bioscience, USA) and internalization was observed. As a scan condition, measurements were performed at a magnification of 100 or 200 times for 24 hours at an interval of 30 minutes, but 4 images were scanned for each well by time. The scanned image was edited in the IncuCyte ZOOM 2016B program and analyzed using the one phase association function among the non-linear fit of Graphpad PRISM (FIG. 9a). Alternatively, after culturing for at least 24 hours, the red fluorescence intensity was measured on a fluorescence filter (Exitation-627 nm, Emission-660~720 nm) in the Glomax™ Discover system (#GM3000, Promega) (FIG. 9b). Incucyte FabFlour Red reagent has a characteristic that fluorescence is not shown at neutral pH, and red fluorescence is emitted as it becomes acidic pH. The antibody is bound to the cell surface B7-H3 antigen, and then it is endocytosized through the endosome, and when it is fused to the lysosome, strong red fluorescence is emitted because it is exposed to an acidic pH (~4.7) environment. It was found that after treatment with the anti-B7-H3 antibody, the cells with a red color inside the cells were increased over time (Red object count/well or Total Red Object Area, um²/well). From this, it can be seen that B7-H3 on the cell surface is a target for the endocytosis of the antibody and that the endocytosis of the anti-B7-H3 antibody is increased over time.

Example 4-7: Endocytosis of B7-H3 Antigen-Antibody Complex (FabZAP)

Figure 10:
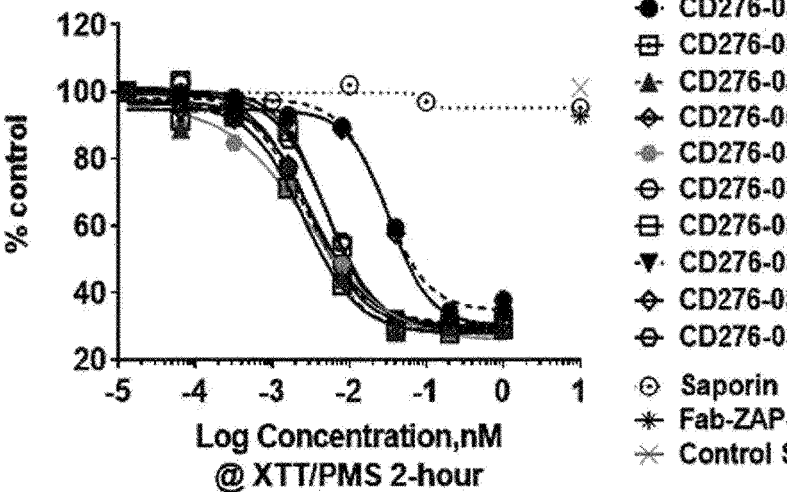
FIG. 10 illustrates a result obtained by measuring the cytotoxicity caused by the endocytosis of the selected B7-H3 antibodies.

The endocytosis of the antibody was identified for its cytotoxic efficacy using the FabZAP antibody internalization kit (#IT-51) of Advanced Targeting System. Saporin is a ribosome inhibitor, and it causes cytotoxicity when it is endocytosized and released. Saporin-conjugated FabZAP protein was diluted in a growth medium to 45 nM, and the antibody was diluted with this solution at a certain ratio, and then allowed to stand at room temperature for 15 minutes to react such that Saporin is conjugated. Saporin to be used as a negative control group was prepared as a 10 uM solution and then prepared by serial dilution at a certain ratio, and Control-SAP, another negative control group, was prepared as a 100 nM solution and then prepared by dilution at a certain ratio. The day before the treatment with each substance, the A498 renal cancer cell line was diluted with a growth medium, plated on a 96-well culture plate at $1×10^3$/ well, and cultured in a $CO_2$ incubator at 37° C. for at least 16 hours. After 72 hours of treatment with the antibody and each substance, 50 uL of XTT substrate solution prepared in PBS was put into each well and reacted in a $CO_2$ incubator at 37° C. for 2 hours, and then absorbance was measured at 450 nm using the GloMax™ Discover System. Saporin substance did not show cytotoxicity because it could not penetrate the cell membrane, and control-SAP without specific antigen binding had no effect on cell growth. In contrast, it was found that the cytotoxic effect of the FabZAP-conjugated anti-B7-H3 antibody was also increased as the concentration of the antibody was increased. This indicates that the anti-B7-H3 antibody bound to B7-H3 expressed on the surface of the A498 cell line was introduced into the cell and cytotoxicity was caused by Saporin released from the lysosome (FIG. 10).

INDUSTRIAL APPLICABILITY

The anti-B7-H3 antibody or antigen binding fragment thereof according to the present invention can bind to human and non-human B7-H3 at a high affinity and can be endocytosized after binding thereto. Thus, the anti-B7-H3 antibody or antigen binding fragment thereof, or the antibody-drug conjugate or the multi-specific antibody comprising the same can be advantageously used for preventing, treating, or diagnosing cancer or tumor, autoimmune disease, or inflammatory disease.

As a specific part of the present invention has been described in detail above, it will be apparent to those of ordinary skill in the art that this specific description is only a preferred embodiment, and the scope of the present invention is not limited thereto. Therefore, it is intended that the substantial scope of the present invention be defined by the appended claims and their equivalents.

The invention claimed is:

1. An anti-B7-H3 antibody or an antigen binding fragment thereof comprising:

a heavy chain CDR (complementarity determining region) 1 of SEQ ID NO: 1, a heavy chain CDR2 of SEQ ID NO: 2, a heavy chain CDR3 of SEQ ID NO: 3, a light chain CDR1 of SEQ ID NO: 4, a light chain CDR2 of SEQ ID NO: 5, and a light chain CDR3 of SEQ ID NO: 6;

a heavy chain CDR1 of SEQ ID NO: 7, a heavy chain CDR2 of SEQ ID NO: 8, a heavy chain CDR3 of SEQ ID NO: 9, a light chain CDR1 of SEQ ID NO: 10, a light chain CDR2 of SEQ ID NO: 11, and a light chain CDR3 of SEQ ID NO: 12;

a heavy chain CDR1 of SEQ ID NO: 13, a heavy chain CDR2 of SEQ ID NO: 14, a heavy chain CDR3 of SEQ ID NO: 15, a light chain CDR1 of SEQ ID NO: 16, a light chain CDR2 of SEQ ID NO: 17, and a light chain CDR3 of SEQ ID NO: 18;

a heavy chain CDR1 of SEQ ID NO: 19, a heavy chain CDR2 of SEQ ID NO: 20, a heavy chain CDR3 of SEQ ID NO: 21, a light chain CDR1 of SEQ ID NO: 22, a light chain CDR2 of SEQ ID NO: 11, and a light chain CDR3 of SEQ ID NO: 23;

a heavy chain CDR1 of SEQ ID NO: 19, a heavy chain CDR2 of SEQ ID NO: 20, a heavy chain CDR3 of SEQ ID NO: 21, a light chain CDR1 of SEQ ID NO: 24, a light chain CDR2 of SEQ ID NO: 11, and a light chain CDR3 of SEQ ID NO: 25;

a heavy chain CDR1 of SEQ ID NO: 19, a heavy chain CDR2 of SEQ ID NO: 20, a heavy chain CDR3 of SEQ ID NO: 21, a light chain CDR1 of SEQ ID NO: 26, a light chain CDR2 of SEQ ID NO: 11, and a light chain CDR3 of SEQ ID NO: 27;

a heavy chain CDR1 of SEQ ID NO: 19, a heavy chain CDR2 of SEQ ID NO: 20, a heavy chain CDR3 of SEQ ID NO: 21, a light chain CDR1 of SEQ ID NO: 28, a light chain CDR2 of SEQ ID NO: 5, and a light chain CDR3 of SEQ ID NO: 29;

a heavy chain CDR1 of SEQ ID NO: 19, a heavy chain CDR2 of SEQ ID NO: 20, a heavy chain CDR3 of SEQ ID NO: 21, a light chain CDR1 of SEQ ID NO: 30, a light chain CDR2 of SEQ ID NO: 31, and a light chain CDR3 of SEQ ID NO: 32;

a heavy chain CDR1 of SEQ ID NO: 19, a heavy chain CDR2 of SEQ ID NO: 20, a heavy chain CDR3 of SEQ ID NO: 21, a light chain CDR1 of SEQ ID NO: 33, a light chain CDR2 of SEQ ID NO: 11, and a light chain CDR3 of SEQ ID NO: 34; or a heavy chain CDR1 of SEQ ID NO: 19, a heavy chain CDR2 of SEQ ID NO: 20, a heavy chain CDR3 of SEQ ID NO: 21, a light chain CDR1 of SEQ ID NO: 35, a light chain CDR2 of SEQ ID NO: 11, and a light chain CDR3 of SEQ ID NO: 36.

2. The anti-B7-H3 antibody or antigen binding fragment thereof according to claim 1, comprising a heavy chain variable region of SEQ ID NO: 37, 39, 41, or 43.

3. The anti-B7-H3 antibody or antigen binding fragment thereof according to claim 1, comprising a light chain variable region of SEQ ID NO: 38, 40, 42, 44, 45, 46, 47, 48, 49, or 50.

4. A nucleic acid encoding the anti-B7-H3 antibody or antigen binding fragment thereof according to claim 1.

5. A recombinant expression vector comprising the nucleic acid according to claim 4.

6. A cell transformed with the recombinant expression vector according to claim 5.

7. The cell according to claim 6, which is selected from the group consisting of animal cells, plant cells, yeast cells, E. coli cells and insect cells.

8. The cell according to claim 6, which is selected from the group consisting of COS-7 (monkey kidney cells 7) cells, NS0 cells, SP2/0 cells, CHO (Chinese hamster ovary) cells, W138 cells, BHK (baby hamster kidney) cells, MDCK cells, myeloma cell lines, HuT 78 cells, HEK293 cells, and the cells of E. coli, Bacillus subtilis, Streptomyces sp., Pseudomonas sp., Proteus mirabilis, Staphylococcus sp., Aspergillus sp., Pichia pastoris, Saccharomyces cerevisiae, Schizosaccharomyces sp., and Neurospora crassa.

9. A method for preparing an anti-B7-H3 antibody or an antigen binding fragment thereof, the method comprising:

(i) culturing the cell according to claim 6; and (ii) recovering an anti-B7-H3 antibody or an antigen binding fragment thereof from the resulting cell culture solution.

10. A multi-specific antibody comprising the antibody or antigen binding fragment thereof according to claim 1.

11. A pharmaceutical composition for treating cancer or tumor, an autoimmune disease, or an inflammatory disease, comprising the anti-B7-H3 antibody or antigen binding fragment thereof according to claim 1 as an active ingredient and a pharmaceutically acceptable additive.

12. The pharmaceutical composition according to claim 11, wherein the cancer or tumor is selected from the group consisting of prostate cancer, ovarian cancer, breast cancer, colon cancer, renal cancer, non-small cell lung cancer, pancreatic cancer, head and neck cancer, melanoma, glioblastoma, and neuroblastoma.

13. The pharmaceutical composition according to claim 11, wherein the autoimmune disease or inflammatory disease is selected from the group consisting of asthma, rheumatoid arthritis, and multiple sclerosis.

14. A composition for diagnosing cancer or tumor, an autoimmune disease, or an inflammatory disease, comprising the anti-B7-H3 antibody or antigen binding fragment thereof according to claim 1.

15. A method of treating cancer or tumor, an autoimmune disease, or an inflammatory disease, the method comprising:
administering a therapeutically effective amount of the anti-B7-H3 antibody or antigen binding fragment thereof according to claim 1 to a subject.

* * * * *

```
                          SEQUENCE LISTING

<160> NUMBER OF SEQ ID NOS: 67

<210> SEQ ID NO 1
<211> LENGTH: 8
<212> TYPE: PRT
<213> ORGANISM: Artificial Sequence
<220> FEATURE:
<223> OTHER INFORMATION: CDRH1 of CD276-040F10

<400> SEQUENCE: 1

Gly Tyr Thr Phe Ser Ser Tyr Trp
1               5

<210> SEQ ID NO 2
<211> LENGTH: 8
<212> TYPE: PRT
<213> ORGANISM: Artificial Sequence
<220> FEATURE:
<223> OTHER INFORMATION: CDRH2 of CD276-040F10

<400> SEQUENCE: 2

Ile Asn Pro Gly Asn Gly His Thr
1               5

<210> SEQ ID NO 3
<211> LENGTH: 16
<212> TYPE: PRT
<213> ORGANISM: Artificial Sequence
<220> FEATURE:
<223> OTHER INFORMATION: CDRH3 of CD276-040F10

<400> SEQUENCE: 3

Val Ala Asp Pro Arg Arg Pro Lys Val Pro Thr Ala Leu Phe Val Tyr
1               5                   10                  15

<210> SEQ ID NO 4
<211> LENGTH: 6
<212> TYPE: PRT
<213> ORGANISM: Artificial Sequence
<220> FEATURE:
<223> OTHER INFORMATION: CDRL1 of CD276-040F10

<400> SEQUENCE: 4

Gln Gly Ile Gly Thr Trp
1               5

<210> SEQ ID NO 5
<211> LENGTH: 3
<212> TYPE: PRT
<213> ORGANISM: Artificial Sequence
<220> FEATURE:
```

<223> OTHER INFORMATION: CDRL2 of CD276-040F10

<400> SEQUENCE: 5

Ala Ala Ser
1

<210> SEQ ID NO 6
<211> LENGTH: 9
<212> TYPE: PRT
<213> ORGANISM: Artificial Sequence
<220> FEATURE:
<223> OTHER INFORMATION: CDRL3 of CD276-040F10

<400> SEQUENCE: 6

Gln Gln Ala Ile Asn Phe Pro Ile Thr
1               5

<210> SEQ ID NO 7
<211> LENGTH: 8
<212> TYPE: PRT
<213> ORGANISM: Artificial Sequence
<220> FEATURE:
<223> OTHER INFORMATION: CDRH1 of CD276-051H04

<400> SEQUENCE: 7

Gly Phe Asn Phe His Asp Tyr Ala
1               5

<210> SEQ ID NO 8
<211> LENGTH: 10
<212> TYPE: PRT
<213> ORGANISM: Artificial Sequence
<220> FEATURE:
<223> OTHER INFORMATION: CDRH2 of CD276-051H04

<400> SEQUENCE: 8

Ile Arg His Gln Arg Tyr Gly Gly Thr Thr
1               5                   10

<210> SEQ ID NO 9
<211> LENGTH: 15
<212> TYPE: PRT
<213> ORGANISM: Artificial Sequence
<220> FEATURE:
<223> OTHER INFORMATION: CDRH3 of CD276-051H04

<400> SEQUENCE: 9

Ala Arg Gly Ser Ser Ser Ser Ser Trp Tyr Leu Pro Asn Asp Tyr
1               5                   10                  15

<210> SEQ ID NO 10
<211> LENGTH: 6
<212> TYPE: PRT
<213> ORGANISM: Artificial Sequence
<220> FEATURE:
<223> OTHER INFORMATION: CDRL1 of CD276-051H04

<400> SEQUENCE: 10

Gln Asp Ile Ser Thr Trp
1               5

<210> SEQ ID NO 11
<211> LENGTH: 3
<212> TYPE: PRT
<213> ORGANISM: Artificial Sequence
<220> FEATURE:
<223> OTHER INFORMATION: CDRL2 of CD276-051H04, CD276-039C05

```
<400> SEQUENCE: 11

Lys Ala Ser
1

<210> SEQ ID NO 12
<211> LENGTH: 8
<212> TYPE: PRT
<213> ORGANISM: Artificial Sequence
<220> FEATURE:
<223> OTHER INFORMATION: CDRL3 of CD276-051H04

<400> SEQUENCE: 12

Gln Gln Tyr Asn Arg Phe Trp Thr
1               5

<210> SEQ ID NO 13
<211> LENGTH: 8
<212> TYPE: PRT
<213> ORGANISM: Artificial Sequence
<220> FEATURE:
<223> OTHER INFORMATION: CDRH1 of CD276-033E03

<400> SEQUENCE: 13

Gly Phe Thr Phe Ser Ser Tyr Ala
1               5

<210> SEQ ID NO 14
<211> LENGTH: 8
<212> TYPE: PRT
<213> ORGANISM: Artificial Sequence
<220> FEATURE:
<223> OTHER INFORMATION: CDRH2 of CD276-033E03

<400> SEQUENCE: 14

Ile Ser Gly Ser Gly Gly Ser Arg
1               5

<210> SEQ ID NO 15
<211> LENGTH: 11
<212> TYPE: PRT
<213> ORGANISM: Artificial Sequence
<220> FEATURE:
<223> OTHER INFORMATION: CDRH3 of CD276-033E03

<400> SEQUENCE: 15

Ala Ser His Thr Ile Pro Gly Ala Trp Asp Val
1               5                   10

<210> SEQ ID NO 16
<211> LENGTH: 9
<212> TYPE: PRT
<213> ORGANISM: Artificial Sequence
<220> FEATURE:
<223> OTHER INFORMATION: CDRL1 of CD276-033E03

<400> SEQUENCE: 16

Thr Arg Asp Val Gly Gly Tyr Asn Tyr
1               5

<210> SEQ ID NO 17
<211> LENGTH: 3
<212> TYPE: PRT
<213> ORGANISM: Artificial Sequence
<220> FEATURE:
<223> OTHER INFORMATION: CDRL2 of CD276-033E03
```

```
<400> SEQUENCE: 17

Asp Val Asn
1

<210> SEQ ID NO 18
<211> LENGTH: 10
<212> TYPE: PRT
<213> ORGANISM: Artificial Sequence
<220> FEATURE:
<223> OTHER INFORMATION: CDRL3 of CD276-033E03

<400> SEQUENCE: 18

Ser Ser Tyr Thr Thr Ser Ser Arg Arg Val
1               5                   10

<210> SEQ ID NO 19
<211> LENGTH: 8
<212> TYPE: PRT
<213> ORGANISM: Artificial Sequence
<220> FEATURE:
<223> OTHER INFORMATION: CDRH1 of CD276-039C05

<400> SEQUENCE: 19

Gly Gly Thr Phe Ser Ser Tyr Ala
1               5

<210> SEQ ID NO 20
<211> LENGTH: 8
<212> TYPE: PRT
<213> ORGANISM: Artificial Sequence
<220> FEATURE:
<223> OTHER INFORMATION: CDRH2 of CD276-039C05

<400> SEQUENCE: 20

Ile Ile Pro Ile Leu Gly Ile Ala
1               5

<210> SEQ ID NO 21
<211> LENGTH: 14
<212> TYPE: PRT
<213> ORGANISM: Artificial Sequence
<220> FEATURE:
<223> OTHER INFORMATION: CDRH3 of CD276-039C05

<400> SEQUENCE: 21

Ala Asn Gly Gly Asp Ser Ser Ser Trp Tyr Thr Phe Asp Tyr
1               5                   10

<210> SEQ ID NO 22
<211> LENGTH: 6
<212> TYPE: PRT
<213> ORGANISM: Artificial Sequence
<220> FEATURE:
<223> OTHER INFORMATION: CDRL1 of CD276-039C05

<400> SEQUENCE: 22

Gln Ser Ile Ser Arg Trp
1               5

<210> SEQ ID NO 23
<211> LENGTH: 9
<212> TYPE: PRT
<213> ORGANISM: Artificial Sequence
<220> FEATURE:
<223> OTHER INFORMATION: CDRL3 of CD276-039C05

<400> SEQUENCE: 23
```

```
Gln Gln Tyr Asn Thr Phe Pro Leu Thr
1               5

<210> SEQ ID NO 24
<211> LENGTH: 6
<212> TYPE: PRT
<213> ORGANISM: Artificial Sequence
<220> FEATURE:
<223> OTHER INFORMATION: CDRL1 of CD276-039C05_LS_001E10

<400> SEQUENCE: 24

Gln Thr Ile Asn Ser Trp
1               5

<210> SEQ ID NO 25
<211> LENGTH: 9
<212> TYPE: PRT
<213> ORGANISM: Artificial Sequence
<220> FEATURE:
<223> OTHER INFORMATION: CDRL3 of CD276-039C05_LS_001E10

<400> SEQUENCE: 25

Gln Gln Tyr Asn Ser Tyr Ser Leu Thr
1               5

<210> SEQ ID NO 26
<211> LENGTH: 6
<212> TYPE: PRT
<213> ORGANISM: Artificial Sequence
<220> FEATURE:
<223> OTHER INFORMATION: CDRL1 of CD276-039C05_LS_002A11

<400> SEQUENCE: 26

Gln Asn Ile Asn Ser Trp
1               5

<210> SEQ ID NO 27
<211> LENGTH: 9
<212> TYPE: PRT
<213> ORGANISM: Artificial Sequence
<220> FEATURE:
<223> OTHER INFORMATION: CDRL3 of CD276-039C05_LS_002A11

<400> SEQUENCE: 27

Gln Gln Tyr Asp Ser Asn Pro Leu Thr
1               5

<210> SEQ ID NO 28
<211> LENGTH: 6
<212> TYPE: PRT
<213> ORGANISM: Artificial Sequence
<220> FEATURE:
<223> OTHER INFORMATION: CDRL1 of CD276-039C05_LS_002B07

<400> SEQUENCE: 28

Gln Gly Ile Ser Ser Tyr
1               5

<210> SEQ ID NO 29
<211> LENGTH: 9
<212> TYPE: PRT
<213> ORGANISM: Artificial Sequence
<220> FEATURE:
<223> OTHER INFORMATION: CDRL3 of CD276-039C05_LS_002B07

<400> SEQUENCE: 29
```

Gln Gln Tyr Tyr Ser Phe Pro Leu Thr
1               5

<210> SEQ ID NO 30
<211> LENGTH: 6
<212> TYPE: PRT
<213> ORGANISM: Artificial Sequence
<220> FEATURE:
<223> OTHER INFORMATION: CDRL1 of CD276-039C05_LS_002C07

<400> SEQUENCE: 30

Gln Ser Ile Arg Ser Trp
1               5

<210> SEQ ID NO 31
<211> LENGTH: 3
<212> TYPE: PRT
<213> ORGANISM: Artificial Sequence
<220> FEATURE:
<223> OTHER INFORMATION: CDRL2 of CD276-039C05_LS_002C07

<400> SEQUENCE: 31

Lys Ala Tyr
1

<210> SEQ ID NO 32
<211> LENGTH: 9
<212> TYPE: PRT
<213> ORGANISM: Artificial Sequence
<220> FEATURE:
<223> OTHER INFORMATION: CDRL3 of CD276-039C05_LS_002C07

<400> SEQUENCE: 32

Gln Gln Tyr Asn Thr Ser Pro Leu Thr
1               5

<210> SEQ ID NO 33
<211> LENGTH: 6
<212> TYPE: PRT
<213> ORGANISM: Artificial Sequence
<220> FEATURE:
<223> OTHER INFORMATION: CDRL1 of CD276-039C05_LS_002D03

<400> SEQUENCE: 33

Glu Thr Ile Ser Ser Trp
1               5

<210> SEQ ID NO 34
<211> LENGTH: 9
<212> TYPE: PRT
<213> ORGANISM: Artificial Sequence
<220> FEATURE:
<223> OTHER INFORMATION: CDRL3 of CD276-039C05_LS_002D03

<400> SEQUENCE: 34

Gln Gln Tyr Tyr Ser Tyr Pro Ile Thr
1               5

<210> SEQ ID NO 35
<211> LENGTH: 6
<212> TYPE: PRT
<213> ORGANISM: Artificial Sequence
<220> FEATURE:
<223> OTHER INFORMATION: CDRL1 of CD276-039C05_LS_002H07

<400> SEQUENCE: 35

Gln Ser Ile Asp Asn Trp

```
1               5

<210> SEQ ID NO 36
<211> LENGTH: 9
<212> TYPE: PRT
<213> ORGANISM: Artificial Sequence
<220> FEATURE:
<223> OTHER INFORMATION: CDRL3 of CD276-039C05_LS_002H07

<400> SEQUENCE: 36

Gln Gln Tyr Asp Ser Asn Pro Leu Thr
1               5

<210> SEQ ID NO 37
<211> LENGTH: 123
<212> TYPE: PRT
<213> ORGANISM: Artificial Sequence
<220> FEATURE:
<223> OTHER INFORMATION: VH

<400> SEQUENCE: 37

Gln Val Gln Leu Val Glu Ser Gly Ala Glu Val Lys Lys Pro Gly Ala
1               5                   10                  15

Ser Val Lys Leu Ser Cys Lys Ala Ser Gly Tyr Thr Phe Ser Ser Tyr
            20                  25                  30

Trp Met His Trp Val Arg Gln Ala Pro Gly Gln Arg Leu Glu Trp Met
        35                  40                  45

Gly Glu Ile Asn Pro Gly Asn Gly His Thr Asn Tyr Asn Glu Lys Phe
    50                  55                  60

Lys Ser Arg Val Thr Ile Thr Val Asp Lys Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Val Ala Asp Pro Arg Arg Pro Lys Val Pro Thr Ala Leu Phe Val Tyr
            100                 105                 110

Trp Gly Gln Gly Thr Leu Val Thr Val Ser Ser
        115                 120

<210> SEQ ID NO 38
<211> LENGTH: 107
<212> TYPE: PRT
<213> ORGANISM: Artificial Sequence
<220> FEATURE:
<223> OTHER INFORMATION: VL

<400> SEQUENCE: 38

Asp Ile Gln Met Thr Gln Ser Pro Ser Ser Val Ser Ala Ser Val Gly
1               5                   10                  15

Asp Arg Val Thr Ile Ser Cys Arg Ala Ser Gln Gly Ile Gly Thr Trp
            20                  25                  30

Leu Ala Trp Tyr Gln Gln Lys Pro Gly Lys Ala Pro Arg Leu Leu Ile
        35                  40                  45

Tyr Ala Ala Ser Ser Leu Asp Ser Gly Val Pro Ser Arg Phe Ser Ala
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Ile Asn Phe Pro Ile
                85                  90                  95

Thr Phe Gly Gln Gly Thr Arg Leu Glu Ile Lys
            100                 105
```

-continued

```
<210> SEQ ID NO 39
<211> LENGTH: 124
<212> TYPE: PRT
<213> ORGANISM: Artificial Sequence
<220> FEATURE:
<223> OTHER INFORMATION: VH

<400> SEQUENCE: 39

Gln Val Gln Leu Val Glu Ser Gly Gly Gly Leu Val Gln Pro Gly Arg
1               5                   10                  15

Ser Leu Arg Leu Ser Cys Thr Thr Ser Gly Phe Asn Phe His Asp Tyr
            20                  25                  30

Ala Leu Ser Trp Val Arg Gln Ala Pro Gly Lys Gly Leu Glu Trp Val
        35                  40                  45

Ser Phe Ile Arg His Gln Arg Tyr Gly Gly Thr Thr Gln Tyr Ala Ala
    50                  55                  60

Ser Val Lys Gly Arg Phe Thr Ile Ser Arg Asp Asp Ser Lys Gly Ile
65                  70                  75                  80

Ala Tyr Leu Gln Met Asn Ser Leu Arg Ala Glu Asp Thr Ala Val Tyr
                85                  90                  95

Tyr Cys Ala Arg Gly Ser Ser Ser Ser Ser Trp Tyr Leu Pro Asn Asp
            100                 105                 110

Tyr Trp Gly Gln Gly Thr Leu Val Thr Val Ser Ser
        115                 120

<210> SEQ ID NO 40
<211> LENGTH: 106
<212> TYPE: PRT
<213> ORGANISM: Artificial Sequence
<220> FEATURE:
<223> OTHER INFORMATION: VL

<400> SEQUENCE: 40

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Asp Ile Ser Thr Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Arg Phe Trp Thr
                85                  90                  95

Phe Gly Gln Gly Thr Lys Val Glu Ile Lys
            100                 105

<210> SEQ ID NO 41
<211> LENGTH: 118
<212> TYPE: PRT
<213> ORGANISM: Artificial Sequence
<220> FEATURE:
<223> OTHER INFORMATION: VH

<400> SEQUENCE: 41

Gln Val Gln Leu Val Glu Ser Gly Gly Gly Leu Val Gln Ser Gly Gly
1               5                   10                  15
```

```
Ser Leu Arg Leu Ser Cys Ala Ala Ser Gly Phe Thr Phe Ser Ser Tyr
        20                  25                  30

Ala Met Ser Trp Val Arg Gln Ala Pro Gly Lys Gly Leu Glu Trp Val
            35                  40                  45

Ser Val Ile Ser Gly Ser Gly Gly Ser Arg Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Ser His Thr Ile Pro Gly Ala Trp Asp Val Trp Gly Gln Gly Thr
            100                 105                 110

Leu Val Thr Val Ser Ser
        115
```

<210> SEQ ID NO 42
<211> LENGTH: 110
<212> TYPE: PRT
<213> ORGANISM: Artificial Sequence
<220> FEATURE:
<223> OTHER INFORMATION: VL

<400> SEQUENCE: 42

```
Gln Ser Ala Leu Thr Gln Pro Ala Ser Val Ser Gly Ser Pro Gly Gln
1               5                   10                  15

Ser Ile Thr Ile Ser Cys Thr Gly Thr Thr Arg Asp Val Gly Gly Tyr
            20                  25                  30

Asn Tyr Val Ser Trp Tyr Gln Gln His Pro Gly Lys Ala Pro Lys Leu
            35                  40                  45

Met Ile Tyr Asp Val Asn Asn Arg Pro Ser Gly Val Ser Tyr Arg Phe
        50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Thr Ser
                85                  90                  95

Ser Arg Arg Val Phe Gly Thr Gly Thr Lys Val Thr Val Leu
            100                 105                 110
```

<210> SEQ ID NO 43
<211> LENGTH: 121
<212> TYPE: PRT
<213> ORGANISM: Artificial Sequence
<220> FEATURE:
<223> OTHER INFORMATION: VH

<400> SEQUENCE: 43

```
Gln Val Gln Leu Val Glu Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Leu Gly Ile Ala Asn Tyr Ala Gln Lys Phe
        50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95
```

-continued

Ala Asn Gly Gly Asp Ser Ser Ser Trp Tyr Thr Phe Asp Tyr Trp Gly
                100                     105                 110

Gln Gly Thr Leu Ile Thr Val Ser Ser
        115                 120

<210> SEQ ID NO 44
<211> LENGTH: 107
<212> TYPE: PRT
<213> ORGANISM: Artificial Sequence
<220> FEATURE:
<223> OTHER INFORMATION: VL

<400> SEQUENCE: 44

Asp Ile Gln Met Thr Gln Ser Pro Ser Thr Leu Ser Ala Ser Val Gly
1               5                   10                  15

Asp Lys Leu Thr Leu Thr Cys Arg Ala Ser Gln Ser Ile Ser Arg Trp
                20                  25                  30

Leu Ala Trp Tyr Gln Gln Lys Pro Gly Lys Ala Pro Lys Leu Leu Ile
            35                  40                  45

Tyr Lys Ala Ser Tyr Leu Gln Thr Gly Val Pro Ser Arg Phe Ser Gly
        50                  55                  60

Ser Gly Thr Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Thr Phe Pro Leu
                85                  90                  95

Thr Phe Ala Gly Gly Thr Lys Val Glu Ile Lys
            100                 105

<210> SEQ ID NO 45
<211> LENGTH: 107
<212> TYPE: PRT
<213> ORGANISM: Artificial Sequence
<220> FEATURE:
<223> OTHER INFORMATION: VL

<400> SEQUENCE: 45

Asp Ile Gln Met Thr Gln Ser Pro Ser Thr Leu Ser Ala Ser Val Gly
1               5                   10                  15

Asp Arg Val Asn Ile Thr Cys Arg Ala Ser Gln Thr Ile Asn Ser Trp
                20                  25                  30

Leu Ala Trp Tyr Gln Gln Lys Pro Gly Lys Ala Pro Lys Leu Leu Ile
            35                  40                  45

Tyr Lys Ala Ser Tyr Leu Gln Thr Gly Val Pro Ser Arg Phe Ser Gly
        50                  55                  60

Ser Gly Ala Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Ser Leu
                85                  90                  95

Thr Phe Gly Gly Gly Thr Lys Val Glu Ile Lys
            100                 105

<210> SEQ ID NO 46
<211> LENGTH: 107
<212> TYPE: PRT
<213> ORGANISM: Artificial Sequence
<220> FEATURE:
<223> OTHER INFORMATION: VL

<400> SEQUENCE: 46

-continued

```
Asp Ile Gln Met Thr Gln Ser Pro Ser Thr Leu Ser Ala Ser Val Gly
1               5                   10                  15

Asp Arg Leu Thr Ile Thr Cys Arg Ala Ser Gln Asn Ile Asn Ser Trp
            20                  25                  30

Leu Ala Trp Tyr Gln Gln Lys Pro Gly Lys Ala Pro Lys Leu Leu Ile
        35                  40                  45

Tyr Lys Ala Ser Tyr Leu Gln Thr Gly Val Pro Ser Arg Phe Ser Gly
    50                  55                  60

Ser Gly Ser Gly Thr Glu Phe Thr Leu Thr Ile Thr Ser Leu Gln Pro
65                  70                  75                  80

Asp Asp Phe Ala Ser Tyr Tyr Cys Gln Gln Tyr Asp Ser Asn Pro Leu
                85                  90                  95

Thr Phe Gly Gly Gly Thr Lys Val Glu Ile Lys
            100                 105
```

<210> SEQ ID NO 47
<211> LENGTH: 107
<212> TYPE: PRT
<213> ORGANISM: Artificial Sequence
<220> FEATURE:
<223> OTHER INFORMATION: VL

<400> SEQUENCE: 47

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ser Phe Pro Leu
                85                  90                  95

Thr Phe Gly Gly Gly Thr Lys Val Glu Ile Lys
            100                 105
```

<210> SEQ ID NO 48
<211> LENGTH: 107
<212> TYPE: PRT
<213> ORGANISM: Artificial Sequence
<220> FEATURE:
<223> OTHER INFORMATION: VL

<400> SEQUENCE: 48

```
Asp Ile Gln Met Thr Gln Ser Pro Ser Thr Leu Ser Ala Ser Val Gly
1               5                   10                  15

Asp Arg Val Thr Ile Thr Cys Arg Ala Gly Gln Ser Ile Arg Ser Trp
            20                  25                  30

Leu Ala Trp Tyr Gln Gln Lys Pro Gly Glu Ala Pro Lys Leu Leu Ile
        35                  40                  45

Tyr Lys Ala Tyr Tyr Leu Gln Thr Gly Val Pro Ser Arg Phe Ser Gly
    50                  55                  60

Ser Gly Ala Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Thr Ser Pro Leu
                85                  90                  95
```

Thr Phe Gly Gly Gly Thr Lys Val Glu Ile Lys
            100                     105

<210> SEQ ID NO 49
<211> LENGTH: 107
<212> TYPE: PRT
<213> ORGANISM: Artificial Sequence
<220> FEATURE:
<223> OTHER INFORMATION: VL

<400> SEQUENCE: 49

Asp Ile Gln Met Thr Gln Ser Pro Ser Thr Leu Ser Ala Ser Val Gly
1               5                   10                  15

Asp Arg Val Thr Ile Thr Cys Arg Ala Ser Glu Thr Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Tyr Ser Tyr Pro Ile
                85                  90                  95

Thr Phe Gly Gln Gly Thr Arg Leu Glu Ile Lys
            100                     105

<210> SEQ ID NO 50
<211> LENGTH: 107
<212> TYPE: PRT
<213> ORGANISM: Artificial Sequence
<220> FEATURE:
<223> OTHER INFORMATION: VL

<400> SEQUENCE: 50

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Asp Asn Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Ser Tyr Tyr Cys Gln Gln Tyr Asp Ser Asn Pro Leu
                85                  90                  95

Thr Phe Gly Gly Gly Thr Lys Val Glu Ile Lys
            100                     105

<210> SEQ ID NO 51
<211> LENGTH: 354
<212> TYPE: DNA
<213> ORGANISM: Artificial Sequence
<220> FEATURE:
<223> OTHER INFORMATION: VH

<400> SEQUENCE: 51
caggtgcagc tggtggagtc tgggggaggc ttggtacagt cggggggggtc cctgagactc      60 tcctgtgcag cctctggatt caccttttagc agctatgcca tgagctgggt ccgccaggct     120

```
ccagggaagg ggctggagtg ggtctcagtt attagtggta gtggtggtag cagatactac      180
gcagactccg tgaagggccg gttcaccatc tccagagaca attccaagaa cacgctgtat      240
ctgcaaatga acagtctgag agccgaggac acggccgtgt attactgtgc gagtcatact      300
ataccaggag cttgggatgt ctggggccaa gggacactgg tcaccgtctc ctca            354
```

```
<210> SEQ ID NO 52
<211> LENGTH: 330
<212> TYPE: DNA
<213> ORGANISM: Artificial Sequence
<220> FEATURE:
<223> OTHER INFORMATION: VL

<400> SEQUENCE: 52
cagtctgccc tgactcagcc tgcctccgtg tctgggtctc ctggacagtc gatcaccatc       60
tcctgcactg gaaccacccg tgacgtcggt ggttataact atgtctcctg gtaccaacaa      120 cacccccggca aagcccccaa actcatgatt tatgatgtca ataatcggcc ctcaggggtt      180
tcttatcgct ctctggctc caagtctggc aacacggcct ccctgaccat ctctgggctc       240
caggctgagg acgaggctga ttattactgc agctcatata caaccagcag cagaaagggtc      300 ttcggaactg ggaccaaggt caccgtccta                                        330
```

```
<210> SEQ ID NO 53
<211> LENGTH: 369
<212> TYPE: DNA
<213> ORGANISM: Artificial Sequence
<220> FEATURE:
<223> OTHER INFORMATION: VH

<400> SEQUENCE: 53
caggtgcagc tggtagagtc tgggggctgaa gtgaagaagc ctgggggcttc agtgaagctg      60 tcctgcaagg cttctggcta caccttcagc agctactgga tgcactgggt gcgccaggcc      120
cctggacaac gccttgagtg gatgggagag attaatcctg gcaacggtca tactaactac      180
aacgagaagt tcaagtcacg cgtgacaatc actgtagaca aatccgcgag cacagcctac      240
atggagctca gcagcctgag atctgaggac acggccgtgt attactgtgt tgcagatccg      300
agaaggccta agtaccaac tgctttgttt gtctattggg gccagggaac cctggtcacc      360
gtctcctca                                                              369
```

```
<210> SEQ ID NO 54
<211> LENGTH: 321
<212> TYPE: DNA
<213> ORGANISM: Artificial Sequence
<220> FEATURE:
<223> OTHER INFORMATION: VL

<400> SEQUENCE: 54
gacatccaga tgacccagtc tccatcttcc gtgtctgcat ctgtaggaga cagagtcacc       60
atcagttgtc gggcgagtca gggtattggc acctggttag cctggtatca gcagaagcca      120
ggtaaagccc ctagactctt gatctatgct gcatccagtt tggacagtgg ggtcccatcg      180
agattcagcg ccagtggatc tgggacagat ttcactctca ccatcagcag cctgcagcct      240
gaagattttg caacttacta ctgtcaacag gctatcaatt cccgatcac cttcggccaa      300 gggacacgac tggaaatcaa a                                                 321
```

```
<210> SEQ ID NO 55
```

-continued

```
<211> LENGTH: 372
<212> TYPE: DNA
<213> ORGANISM: Artificial Sequence
<220> FEATURE:
<223> OTHER INFORMATION: VH

<400> SEQUENCE: 55
caggtgcagc tggtggagtc tggggggaggc ttggtacagc caggacggtc cctgagactc      60
tcctgtacaa cctctggatt caatttccat gattatgctc tgtcctgggt ccggcaggct     120
ccagggaagg ggctggaatg ggtgagtttc attagacacc aacgttatgg tgggacaacg     180
cagtacgccg cgtctgtgaa aggcagattc accatctcaa gagacgattc caaaggcatc     240
gcatacctgc aaatgaacag tctgagagcc gaggacacgg ccgtgtatta ctgtgcgaga     300
ggatcttcca gcagcagctg gtaccttcca aatgactact ggggccaggg aaccctggtc     360
accgtctcct ca                                                         372

<210> SEQ ID NO 56
<211> LENGTH: 318
<212> TYPE: DNA
<213> ORGANISM: Artificial Sequence
<220> FEATURE:
<223> OTHER INFORMATION: VL

<400> SEQUENCE: 56
gacatccaga tgacccagtc tccttccacc ctgtctgcat ctgtaggaga cagagtcacc      60
atcacttgcc gggccagtca ggacattagt acctggttgg cctggtatca gcagaagcca     120
gggaaagccc ctaaactcct gatctataag gcgtctagtt tacaaagtgg ggtcccatca     180
agattcagcg gcagtggatc tgggacagaa ttcactctca ctatcagcag cctgcagcct     240
gatgattttg caacttatta ctgccaacag tataataggt tttggacatt cggccaaggg     300
accaaggtgg aaatcaaa                                                   318

<210> SEQ ID NO 57
<211> LENGTH: 363
<212> TYPE: DNA
<213> ORGANISM: Artificial Sequence
<220> FEATURE:
<223> OTHER INFORMATION: VH

<400> SEQUENCE: 57
caggtgcagc tggtggagtc tggggctgag gtgaagaagc ctgggtcctc ggtgaaggtc      60
tcctgcaagg cttctggagg caccttcagc agctatgcta tcagctgggt gcgacaggcc     120
cctggacaag ggcttgagtg gatgggaagg atcatcccta tccttggtat agcaaactac     180
gcacagaagt tccagggcag agtcacgatt accgcggaca atccacgag cacagcctac       240 atggagctga gcagcctgag atctgaggac acggccgtgt attactgtgc gaatggaggg     300
gatagcagca gctggtacac ctttgactac tggggccagg gaaccctgat caccgtctcc     360
tca                                                                   363

<210> SEQ ID NO 58
<211> LENGTH: 321
<212> TYPE: DNA
<213> ORGANISM: Artificial Sequence
<220> FEATURE:
<223> OTHER INFORMATION: VL

<400> SEQUENCE: 58
gacatccaga tgacccagtc tccttccacc ctgtctgcat ctgtaggaga caaactcacc      60
```

-continued

```
ctcacctgcc gggccagtca gagtattagt agatggttgg cctggtatca gcagaaacct    120
ggaaaagccc ctaaactcct catctataag gcatcttatt tacaaactgg ggtcccgtca    180
agattcagcg gcagtggaac tgggacagaa ttcactctca ccatcagcag cctgcagcct    240
gatgattttg cgacttatta ctgccaacaa tataatactt tcccgctcac tttcgccgga    300
gggaccaagg tggaaatcaa a                                              321
```

```
<210> SEQ ID NO 59
<211> LENGTH: 321
<212> TYPE: DNA
<213> ORGANISM: Artificial Sequence
<220> FEATURE:
<223> OTHER INFORMATION: VL

<400> SEQUENCE: 59
gacatccaga tgacccagtc tccttccacc ctgtctgctt ctgtaggaga cagagtcaat     60
atcacttgcc gggccagtca aactattaat agttggttgg cctggtatca gcagaaacca    120
gggaaagccc ctaaactcct catctataag gcatcttatt tacaaactgg ggtcccgtca    180
agattcagcg gcagtggagc tgggacagaa ttcactctca ccatcagcag cctgcagcct    240
gatgattttg cgacttatta ctgccaacag tataatagtt attctcttac tttcggcgga    300
gggaccaagg tagagatcaa a                                              321
```

```
<210> SEQ ID NO 60
<211> LENGTH: 321
<212> TYPE: DNA
<213> ORGANISM: Artificial Sequence
<220> FEATURE:
<223> OTHER INFORMATION: VL

<400> SEQUENCE: 60
gacatccaga tgacccagtc tccttccacc ctgtctgcat ctgttggtga cagactcacc     60
atcacttgtc gggccagtca gaatattaat agttggttgg cctggtatca gcagaaacct    120
ggaaaagccc ctaaactcct catctataag gcatcttatt tacaaactgg ggtcccgtca    180
agattcagcg gcagtggatc tgggacagaa ttcaccctca ccatcaccag cctgcagcct    240
gacgattttg caagttatta ctgccaacag tatgacagta atccgctcac tttcggcgga    300
gggaccaagg tggaaatcaa a                                              321
```

```
<210> SEQ ID NO 61
<211> LENGTH: 321
<212> TYPE: DNA
<213> ORGANISM: Artificial Sequence
<220> FEATURE:
<223> OTHER INFORMATION: VL

<400> SEQUENCE: 61
gacatccaga tgacccagtc tccatcctcc ctgtctgcat ctgtaggaga cagagtcacc     60
atcacttgcc gggccagtca gggcattagc agttatttag cctggtatca gcaaaaacca    120
gggaaagccc ctaagctcct gatctatgct gcatccactt tgcaaagtgg ggtcccatca    180
aggttcagcg gcagtggatc tgggacggat ttcactctca ccatcagcag cctgcagcct    240
gaagattttg caacttatta ctgccaacag tattattctt ttccgctcac tttcggcgga    300
gggaccaagg tggaaatcaa a                                              321
```

```
<210> SEQ ID NO 62
```

```
<211> LENGTH: 321
<212> TYPE: DNA
<213> ORGANISM: Artificial Sequence
<220> FEATURE:
<223> OTHER INFORMATION: VL

<400> SEQUENCE: 62
gacatccaga tgacccagtc tccttctacc ctgtctgctt ctgtcgggga cagagtcacc      60
atcacttgcc gggccggtca gagtattcgt agttggctgg cctggtatca gcagaaacca     120
ggggaggccc ctaaactcct catctataag gcatattatt tacaaactgg ggtcccgtca     180
agattcagcg gcagtggagc tgggacagaa ttcactctca ccatcagcag cctgcagcct     240
gatgattttg cgacttatta ctgccaacaa tataatactt cccccctcac tttcggcgga     300
gggaccaagg tggaaatcaa a                                                321

<210> SEQ ID NO 63
<211> LENGTH: 321
<212> TYPE: DNA
<213> ORGANISM: Artificial Sequence
<220> FEATURE:
<223> OTHER INFORMATION: VL

<400> SEQUENCE: 63
gacatccaga tgacccagtc tccttccacc ctgtctgcat ctgtaggaga cagagtcacc      60
atcacttgcc gggccagtga gactattagt agctggttgg cctggtatca gcagaaacca     120
gggaaagccc ctaagctcct gatctataag gcatctagtt tacaaagtgg ggtcccatca     180
aggttcagcg gcagcggatc tgggacagaa ttcactctca ccatcagcag cctgcagcct     240
gatgattttg caacttatta ctgccaacag tattatagtt atccgatcac cttcggccaa     300
gggacacgac tggagatcaa a                                                321

<210> SEQ ID NO 64
<211> LENGTH: 321
<212> TYPE: DNA
<213> ORGANISM: Artificial Sequence
<220> FEATURE:
<223> OTHER INFORMATION: VL

<400> SEQUENCE: 64
gacatccaga tgacccagtc tccttccacc ctgtctgcat ctgttggaga cagagtcacc      60
atcacttgcc gggccagtca gagtattgat aattggttgg cctggtatca gcagaagcca     120
gggaaagccc ctaagctcct gatctataag gcgtctagtt tacaaagtgg ggtcccatca     180
aggttcagcg gcagtggatc tgggacagaa ttcactctca ccatcagcag cctgcagcct     240
gacgattttg caagttatta ctgccaacag tatgacagta atccgctcac tttcggcgga     300
gggaccaagg tggaaatcaa a                                                321

<210> SEQ ID NO 65
<211> LENGTH: 438
<212> TYPE: PRT
<213> ORGANISM: Artificial Sequence
<220> FEATURE:
<223> OTHER INFORMATION: B7-H3

<400> SEQUENCE: 65

Leu Glu Val Gln Val Pro Glu Asp Pro Val Val Ala Leu Val Gly Thr
1               5                   10                  15

Asp Ala Thr Leu Cys Cys Ser Phe Ser Pro Glu Pro Gly Phe Ser Leu
            20                  25                  30
```

```
Ala Gln Leu Asn Leu Ile Trp Gln Leu Thr Asp Thr Lys Gln Leu Val
        35              40                  45

His Ser Phe Ala Glu Gly Gln Asp Gln Gly Ser Ala Tyr Ala Asn Arg
        50              55                  60

Thr Ala Leu Phe Pro Asp Leu Leu Ala Gln Gly Asn Ala Ser Leu Arg
65              70                  75                  80

Leu Gln Arg Val Arg Val Ala Asp Glu Gly Ser Phe Thr Cys Phe Val
                85                  90                  95

Ser Ile Arg Asp Phe Gly Ser Ala Ala Val Ser Leu Gln Val Ala Ala
                100             105                 110

Pro Tyr Ser Lys Pro Ser Met Thr Leu Glu Pro Asn Lys Asp Leu Arg
                115             120                 125

Pro Gly Asp Thr Val Thr Ile Thr Cys Ser Ser Tyr Gln Gly Tyr Pro
        130             135                 140

Glu Ala Glu Val Phe Trp Gln Asp Gly Gln Gly Val Pro Leu Thr Gly
145             150                 155                 160

Asn Val Thr Thr Ser Gln Met Ala Asn Glu Gln Gly Leu Phe Asp Val
                165             170                 175

His Ser Ile Leu Arg Val Val Leu Gly Ala Asn Gly Thr Tyr Ser Cys
        180             185                 190

Leu Val Arg Asn Pro Val Leu Gln Gln Asp Ala His Ser Ser Val Thr
        195             200                 205

Ile Thr Pro Gln Arg Ser Pro Thr Gly Ala Val Glu Val Gln Val Pro
        210             215                 220

Glu Asp Pro Val Val Ala Leu Val Gly Thr Asp Ala Thr Leu Arg Cys
225             230                 235                 240

Ser Phe Ser Pro Glu Pro Gly Phe Ser Leu Ala Gln Leu Asn Leu Ile
                245             250                 255

Trp Gln Leu Thr Asp Thr Lys Gln Leu Val His Ser Phe Thr Glu Gly
        260             265                 270

Arg Asp Gln Gly Ser Ala Tyr Ala Asn Arg Thr Ala Leu Phe Pro Asp
        275             280                 285

Leu Leu Ala Gln Gly Asn Ala Ser Leu Arg Leu Gln Arg Val Arg Val
        290             295                 300

Ala Asp Glu Gly Ser Phe Thr Cys Phe Val Ser Ile Arg Asp Phe Gly
305             310                 315                 320

Ser Ala Ala Val Ser Leu Gln Val Ala Ala Pro Tyr Ser Lys Pro Ser
                325             330                 335

Met Thr Leu Glu Pro Asn Lys Asp Leu Arg Pro Gly Asp Thr Val Thr
        340             345                 350

Ile Thr Cys Ser Ser Tyr Arg Gly Tyr Pro Glu Ala Glu Val Phe Trp
        355             360                 365

Gln Asp Gly Gln Gly Val Pro Leu Thr Gly Asn Val Thr Thr Ser Gln
        370             375                 380

Met Ala Asn Glu Gln Gly Leu Phe Asp Val His Ser Val Leu Arg Val
385             390                 395                 400

Val Leu Gly Ala Asn Gly Thr Tyr Ser Cys Leu Val Arg Asn Pro Val
                405             410                 415

Leu Gln Gln Asp Ala His Gly Ser Val Thr Ile Thr Gly Gln Pro Met
                420             425                 430

Thr Phe Pro Pro Glu Ala
        435
```

-continued

```
<210> SEQ ID NO 66
<211> LENGTH: 25
<212> TYPE: DNA
<213> ORGANISM: Artificial Sequence
<220> FEATURE:
<223> OTHER INFORMATION: Primer

<400> SEQUENCE: 66
ctggaggtcc aggtccctga agacc                                          25

<210> SEQ ID NO 67
<211> LENGTH: 25
<212> TYPE: DNA
<213> ORGANISM: Artificial Sequence
<220> FEATURE:
<223> OTHER INFORMATION: Primer

<400> SEQUENCE: 67
ggcctctggg gggaatgtca taggc                                          25
```